(12) United States Patent
Dodd et al.

(10) Patent No.: US 7,259,233 B2
(45) Date of Patent: Aug. 21, 2007

(54) CHRONIC TREATMENT REGIMEN USING GLUCAGON-LIKE INSULINOTROPIC PEPTIDES

(75) Inventors: Steven Witt Dodd, Zionsville, IN (US); Kenneth Francis Mace, Fishers, IN (US); Michael Ernst Trautmann, Hamburg (DE)

(73) Assignee: Eli Lilly and Company, Indianapolis, IN (US)

( * ) Notice: Subject to any disclaimer, the term of this patent is extended or adjusted under 35 U.S.C. 154(b) by 284 days.

(21) Appl. No.: 10/450,124

(22) PCT Filed: Dec. 7, 2001

(86) PCT No.: PCT/US01/44698

§ 371 (c)(1),
(2), (4) Date: Jun. 10, 2003

(87) PCT Pub. No.: WO02/47716

PCT Pub. Date: Jun. 20, 2002

(65) Prior Publication Data

US 2004/0053819 A1    Mar. 18, 2004

Related U.S. Application Data

(60) Provisional application No. 60/255,251, filed on Dec. 13, 2000, provisional application No. 60/295,655, filed on Jun. 4, 2001, provisional application No. 60/298,652, filed on Jun. 15, 2001.

(51) Int. Cl.
    *C07K 14/605* (2006.01)
(52) U.S. Cl. .................. 530/308; 530/324; 530/399; 514/12
(58) Field of Classification Search ............... 530/324, 530/399, 308; 514/12
See application file for complete search history.

(56) References Cited

U.S. PATENT DOCUMENTS

| 5,512,549 | A | * | 4/1996 | Chen et al. .................. 514/12 |
| 5,977,071 | A | | 11/1999 | Galloway et al. |
| 6,458,924 | B2 | * | 10/2002 | Knudsen et al. ............. 530/324 |
| 6,504,005 | B1 | * | 1/2003 | Fridkin et al. ............... 530/303 |
| 6,583,111 | B1 | * | 6/2003 | DiMarchi et al. .............. 514/2 |
| 6,747,006 | B2 | * | 6/2004 | Efendic ........................ 514/12 |
| 6,849,708 | B1 | * | 2/2005 | Habener .................... 530/308 |
| 6,884,579 | B2 | * | 4/2005 | Holst et al. ..................... 435/6 |
| 2003/0220274 | A1 | * | 11/2003 | Oh et al. ...................... 514/44 |

FOREIGN PATENT DOCUMENTS

| EP | 0 926 159 | 6/1999 |
| EP | 1 076 066 | 2/2001 |
| WO | WO99 43708 | 9/1999 |
| WO | WO 02 47715 | 6/2002 |
| WO | WO 02 48183 | 6/2002 |

OTHER PUBLICATIONS

Schirra J Journal of Clinical Investigation 101 (7) 1421-30, 1998.*
Gutniak M. K. Diabetes Care 19 (8) 843-8, 1996.*
Yen T. T. (Archives Internationales de Pharmacodynamie et de Therapie 310,162-74, 1991).*
Koike D (Gastroenterology 108(4), 1221-9, 1995).*
Dunbar J. C. (Diabetologia 14(1), 53-58, 1978).*
Schmidt P. T. (Regulatory Peptides 116 (1-3) 21-5, 2003).*
Deacon, C. F., et al. "Depeptidyl Peptidase IV Resistant Analogues of Glucagon-like Peptide-1 Which Have Extended Metabolic Stability and Improved Biological Activity," Diabetologia, Berlin, DE, vol. 41, 1998, pp. 271-278. XP002202152.
Greig, N. H., et al. "Once Daily Injection of Exendin-4 to Diabetic Mice Achieves Long-Term Beneficial Effects on Blood Glucose Concentrations," Diabetologia, Berlin, DE, vol. 42, No. 1, Jan. 1999, pates 45-50, XP 000971927.
Knudsen, L. B., et al, "Potent Derivatives of Glucagon-Like Peptide-1 with Pharmacokinetic Properties Suitable for Once Daily Administration," Journal of Medicinal Chemistry, American Chemical Society. Washington, US, vol. 43, No. 9 (May 4, 2000), pp. 1664-1669, XP 002222050.

* cited by examiner

*Primary Examiner*—David Lukton
(74) *Attorney, Agent, or Firm*—Alejandro Martinez; Gregory A. Cox

(57) ABSTRACT

The present invention encompasses a method of treating a disease by maintaining chronic steady state serum levels of a GLP-1 compound within a specified range.

8 Claims, 4 Drawing Sheets

CHRONIC TREATMENT REGIMEN USING GLUCAGON-LIKE INSULINOTROPIC PEPTIDES

Figure 1:
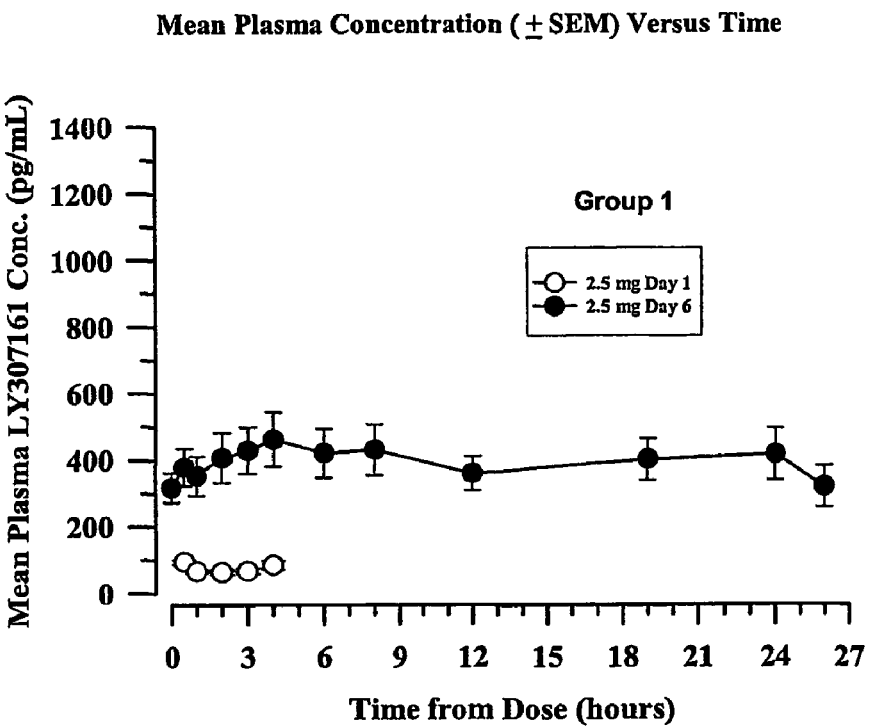
Figure 1:
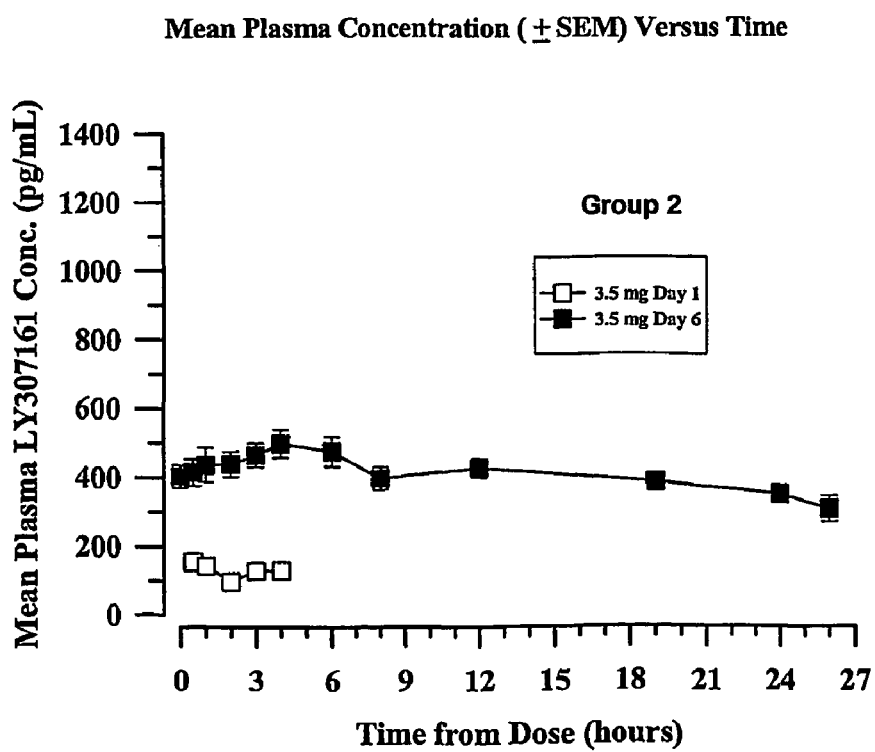

This is the national phase application, under 35 USC 371, for PCT/US01/44698, filed Dec. 7, 2001, which claims the priority of U.S. provisional application Nos. 60/298,652, filed Jun. 15, 2001, 60/295,655 filed Jun. 4, 2001, and 60/255,251 filed Dec. 13, 2000.

1. Field of the Invention

The present invention relates to a chronic treatment regimen using glucagon-like insulinotropic peptides in pharmaceutical articles of manufacture and methods.

2. Background Information

The intestinal hormone glucagon-like peptide-1 (GLP-1) shows great promise as a treatment for type 2 diabetes due to its ability to stimulate insulin secretion, lower glucagon secretion, inhibit gastric emptying, enhance glucose utilization, and induce appetite suppression and weight loss. Further, pre-clinical studies suggest that GLP-1 may also act to prevent the β-cell deterioration that occurs as the disease progresses. Perhaps the most salient characteristic of GLP-1 is its ability to stimulate insulin secretion without the associated risk of hypoglycemia that is often seen when using insulin therapy and some types of oral therapies. When blood glucose levels drop to a certain threshold level, GLP-1 is not active.

However, the usefulness of therapy involving GLP-1 peptides has been limited by the fact that GLP-1(1-37) is poorly active, and the two naturally occurring truncated peptides, GLP-1(7-37)OH and GLP-1(7-36)NH$_2$, have extremely short half-lives and are rapidly cleared from the circulation. Thus, research related to GLP-1 has focused on the development of GLP-1 analogs, GLP-1 derivatives, and formulations thereof which provide a more extended time action. Despite much progress in this area of development, there are no published papers reporting on clinical data in humans using long-acting GLP-1 analogs or derivatives. Until the present invention, it has been unclear whether steady state levels of a GLP-1 compound with a particular potency can be safely maintained for a lengthy course of treatment and continue to provide the benefits associated with the activities that have been elucidated for endogenous GLP-1.

Some short-term clinical studies with native GLP-1 which require continuous infusion or frequent dosing suggest that high concentrations of GLP-1 cause frequent nausea and vomiting. This has raised concern among clinicians that these undesired effects will limit the dosage and thus, limit the efficacy even though the drug inherently may be capable of producing a greater effect.

There are several published clinical studies involving administration of native GLP-1(7-37)OH to patients by i.v. or subcutaneous continuous infusion. See Naslund, et al. (1999) *Am. J. Phys.* 277(3):1-14; Deacon, et al. (1995) *Diabetes* 44:1126-1131; Toft-Nielsen, et al. (1999) *Diabetes Care* 22(7):1137-1143. The published studies consistently use a dose between about 0.75 pmol/kg/min and 2.4 pmol/kg/min for short periods of time. However, because GLP-1(7-37)OH is rapidly degraded upon exposure to plasma, it is not always clear what levels of intact/active GLP-1 peptide are present in the plasma at a given time point.

Naslund, et al., nevertheless, were able to predict plasma levels of intact GLP-1(7-37)OH after continuous administration at a rate of 0.75 pmol/kg/min for 180 min. The authors used a sandwich radioimmunoassy to detect both N-terminally degraded and intact GLP-1(7-37)OH. Plasma levels of intact GLP-1 were approximately 20 picomolar for the last 120 min. of treatment. Using a similar assay, Toft-Nielsen et al. reported intact GLP-1 levels of approximately 10.2 picomolar and 22.5 picomolar after administration of 1.2 pmol/kg/min and 2.4 pmol/kg/min, respectively.

These studies, however, have not answered the question whether plasma levels of intact and active GLP-1 can be achieved to achieve therapeutic benefit while at the same time avoiding or minimizing side effects such as nausea and vomiting. Similarly, these studies do not indicate whether plasma levels of active GLP-1 should be relatively flat during treatment or whether peaks and valleys, which would mimic the physiological state, would be preferred. Thus, despite considerable progress, there remains a need to discover and understand what treatment regimen leads to effective long-term therapy and whether such treatment can be maintained with minimal side effects such as nausea and vomiting.

Applicants have discovered that maintaining continuous plasma levels of a GLP-1 compound in a specific range provides effective treatment. It is believed that the absence of peaks and valleys avoids or minimizes side effects such as nausea and vomiting. Accordingly, the present invention provides a chronic treatment regimen which comprises maintaining continuous plasma levels of a GLP-1 compound within a certain range that avoids or minimizes side effects such as nausea and vomiting. The plasma levels encompassed by the present invention provide optimal blood glucose control. Furthermore, this treatment regimen provides long-term positive health effects including the inducement of weight loss, improvement of β cell function, activation of dormant β cells, differentiation of cells into β cells, β cell proliferation, and the maintenance of organ function.

The present invention encompasses a method of normalizing blood glucose levels, preventing β cell deterioration, inducing weight loss, or treating a condition selected from the group consisting of: hyperglycemia, type 2 diabetes, obesity, stroke, myocardial infarction, catabolic changes that occur after surgery, and irritable bowel syndrome, which comprises maintaining chronic steady state plasma levels between about 60 picomoles/liter and about 200 picomoles/liter of a GLP-1 analog or derivative in a biologically active form having an in vitro potency within two-fold the in vitro potency of Val$^8$-GLP-1(7-37)OH wherein the GLP-1 analog or derivative is administered by subcutaneous injection no more than once or twice every 24 hours.

The present invention also encompasses a method of normalizing blood glucose levels, preventing β cell deterioration, inducing weight loss, or treating a condition selected from the group consisting of: hyperglycemia, type 2 diabetes, obesity, stroke, myocardial infarction, catabolic changes that occur after surgery, and irritable bowel syndrome, which comprises maintaining chronic steady state plasma levels between about 60/X picomolar and about 200/X picomolar of a GLP-1 analog or derivative in a biologically active form wherein X is the in vitro potency of the GLP-1 analog or derivative relative to Val$^8$-GLP-1(7-37)OH which is a given a value of 1 and wherein the GLP-1 analog or derivative is administered by subcutaneous injection no more than once or twice every 24 hours.

The present invention also encompasses use of a GLP-1 analog or derivative having an in vitro potency within 2-fold that of Val$^8$-GLP-1(7-37)OH for the manufacture of a medicament for normalizing blood glucose, preserving β cells, inducing weight loss, or treating a condition selected from the group consisting of: hyperglycemia, type 2 diabetes, stroke, myocardial infarction, catabolic changes that occur after surgery, obesity, and irritable bowel syndrome which comprises maintaining chronic steady state plasma levels of the GLP-1 analog or derivative between about 60 picomolar and about 200 picomolar and wherein the GLP-1 analog or derivative is administered by subcutaneous injection not more the once or twice every 24 hours.

The present invention also encompasses use of a GLP-1 analog or derivative for the manufacture of a medicament for normalizing blood glucose, preserving β cells, inducing weight loss, or treating a condition selected from the group consisting of: hyperglycemia, type 2 diabetes, stroke, myocardial infarction, catabolic changes that occur after surgery, obesity, and irritable bowel syndrome which comprises maintaining chronic steady state plasma levels of the GLP-1 analog or derivative between about 60/X picomolar and about 200/X picomolar wherein X is the in vitro potency of the GLP-1 analog or derivative relative to Val$^8$-GLP-1(7-37)OH which is given a reference value of 1 and wherein the GLP-1 analog or derivative is administered by subcutaneous injection no more than once or twice every 24 hours.

The invention also encompasses an article of manufacture for human pharmaceutical use comprising a container; a dosage form comprising an amount of a GLP-1 analog or derivative having an in vitro potency within two-fold that of Val$^8$-GLP-1(7-37)OH, and a package insert that provides for administration of the dosage form that results in maintaining GLP-1 analog or derivative plasma levels between about 60 picomolar and about 200 picomolar.

FIG. 1: Graphs representing the mean (+/−SEM) plasma Val$^8$-GLP-1(7-37)OH concentrations following once-daily administration of placebo (baseline), 2.5 mg (Group 1), and 3.5 mg (Group 2) of Val$^8$-GLP-1(7-37)OH to patients with type 2 diabetes.

Figure 2:
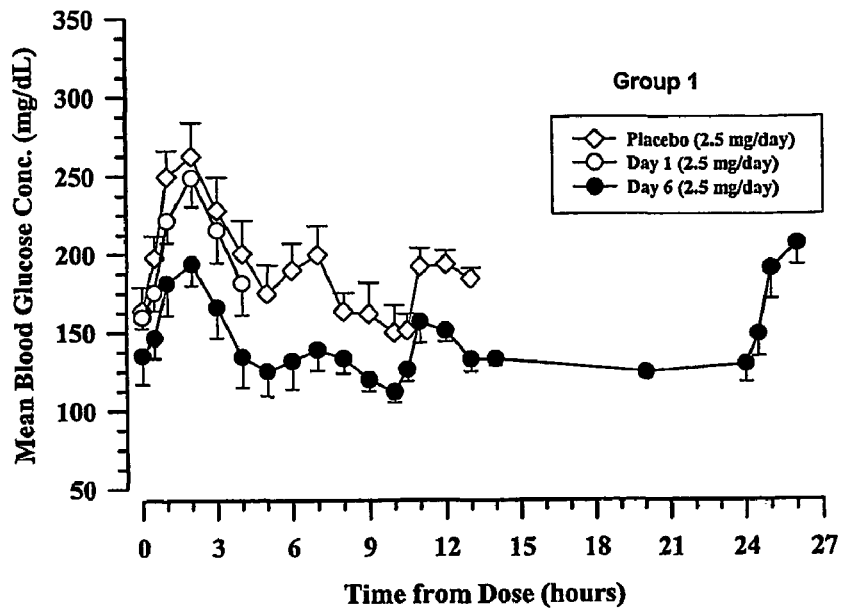
Figure 2:
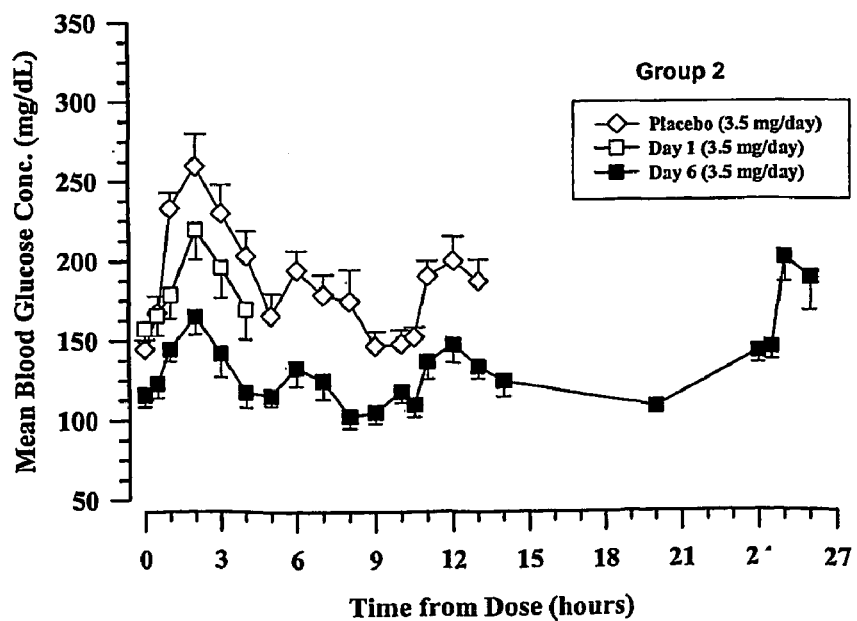

FIG. 2: Graphs representing the mean (+/−SEM) glucose concentrations following once-daily administration of placebo (baseline), 2.5 mg (Group 1), and 3.5 mg (Group 2) of Val$^8$-GLP-1(7-37)OH to patients with type 2 diabetes.

Figure 3:
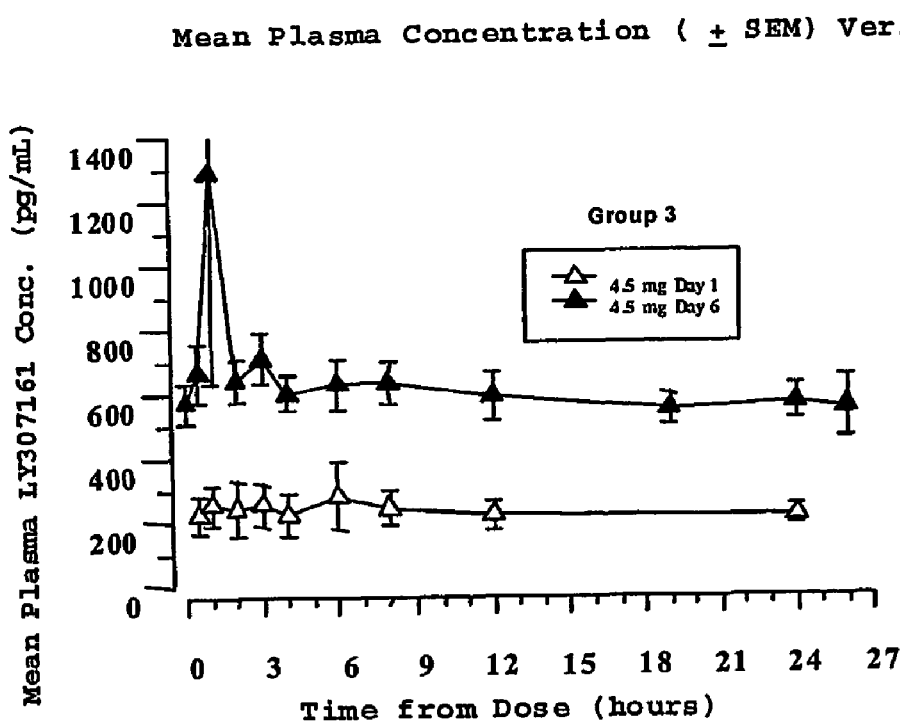
Figure 3:
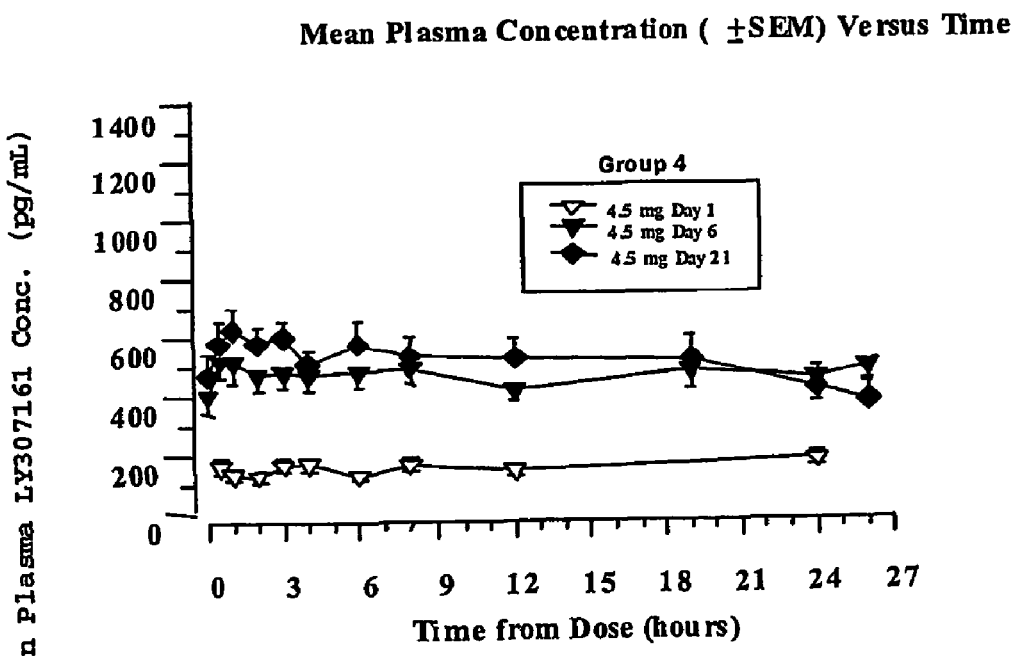

FIG. 3: Graphs representing the mean (+/−SEM) plasma Val$^8$-GLP-1(7-37)OH concentrations following once-daily administration of placebo (baseline) and 4.5 mg (Groups 3 and 4) of Val$^8$-GLP-1(7-37)OH to patients with type 2 diabetes.

Figure 4:
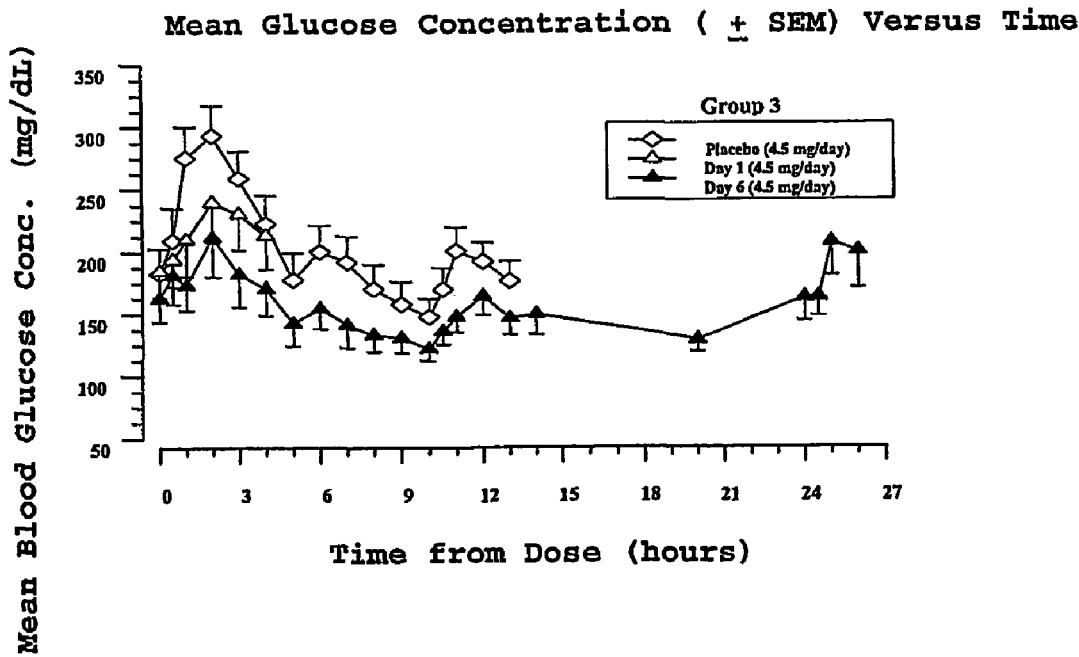
Figure 4:
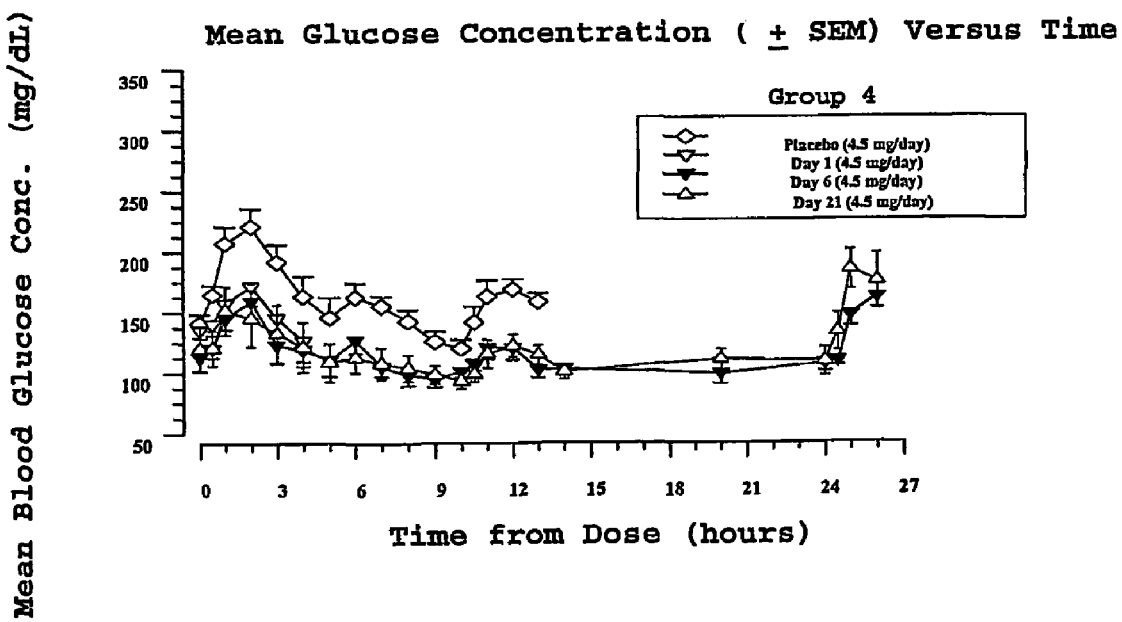

FIG. 4: Graphs representing the mean (+/−SEM) glucose concentrations following once-daily administration of placebo (baseline) and 4.5 mg (Groups 3 and 4) of Val$^8$-GLP-1(7-37)OH to patients with type 2 diabetes.

For purposes of the present invention as disclosed and described herein, the following terms and abbreviations are defined as follows.

A "treatment regimen" is the administration of a GLP-1 compound such that optimum plasma levels are chronically maintained. The GLP-1 compounds used for the regimen of the present invention exert their biological effects by acting at a receptor referred to as the GLP-1 receptor. Subjects with diseases and/or conditions that respond favorably to GLP-1 receptor stimulation or to the administration of GLP-1 compounds can therefore be treated with the regimen of the present invention.

Thus, this regimen provides a variety of positive effects including but not limited to treating hyperglycemia, maintaining blood glucose control, treating type 2 diabetes, treating obesity, inducing weight loss, treating stroke, treating myocardial infarction, treating catabolic changes that occur after surgery or for other reasons, treating irritable bowel syndrome, preventing β-cell deterioration, inducing β-cell proliferation, stimulating insulin gene transcription, up-regulating IDX-1/PDX-1 or other growth factors, improving β-cell function, activating dormant β-cells, differentiating cells into β-cells, and/or β cell replication. Positive effects that result from maintaining blood plasma levels within a specific range over extended time periods include an amelioration of the symptom(s) associated with the disease or condition being treated, a delay in the onset of symptoms associated with the disease or condition being treated, increased longevity compared with the absence of the treatment, and/or a greater quality of life compared with the absence of the treatment. Further benefits provided by the treatment regimen of the present invention which relate to the treatment of type 2 diabetes and associated hyperglycemia include enhanced convenience due to the elimination or reduction of blood glucose self-monitoring and administration of drug that need not be timed with meals.

"Chronic therapy" refers to maintaining blood plasma levels of active GLP-1 compounds within a specific range for a course of therapy. The specified range corresponds to plasma levels of active GLP-1 compounds that provide optimal efficacy and yet do not cause or at least minimize side effects such as nausea and vomiting. A planned course of therapy will differ depending on the condition or disease being treated. For example, a planned course of therapy for a type 2 diabetic wherein oral medications are no longer able to control blood glucose levels would encompass that time period wherein the patient has adequate β cell function to respond to GLP-1 receptor stimulation. A planned course of therapy for an obese patient or a patient desiring to lose weight would encompass that time period until the patient has reached a normal weight based on the patient's height and build. A planned course of therapy may also have a prophylactic goal such as to prevent the progression of type 2 diabetes, the development of diabetes, impaired glucose tolerance, syndrome x, or to prevent weight gain. This type of therapy could potentially last a patient's lifetime.

"Chronic" generally refers to regular administration for an extended period preferably not more frequently than twice daily, most preferably not more than once daily. However, chronic administration as used herein may encompass other regimens in addition to once or twice daily dosing. For example, chronic administration encompasses administration of a sustained release formulation that provides sufficient therapeutic blood plasma levels on a regular basis. Such administration may include administration once a week, once a month, or even less frequently. Contrary to acute or on-demand administration, chronic administration does not link administration of drug to events such as meals, results of home glucose monitoring, or need for appetite suppression.

"Insulinotropic activity" refers to the ability to stimulate insulin secretion in response to elevated glucose levels, thereby causing glucose uptake by cells and decreased plasma glucose levels. Insulinotropic activity can be assessed by methods known in the art, including using in vivo experiments and in vitro assays that measure GLP-1 receptor binding activity or receptor activation, e.g., assays employing pancreatic islet cells or insulinoma cells, as described in EP 619,322 to Gelfand, et al., and U.S. Pat. No. 5,120,712, respectively. The entire teachings of these references are incorporated herein by reference. Insulinotropic activity is routinely measured in humans by measuring insulin levels or C-peptide levels.

"Container" means any receptacle and closure suitable for storing, shipping, dispensing, and/or handling a pharmaceutical product.

"Packaging" means a customer-friendly device allowing convenient administration and/or ancillary devices that aid in delivery, education, and/or administration. The packaging may improve GLP-1 compound administration to the patient, reduce or improve educational instruction time for the patient, provide a platform for improved health economic studies, and/or limit distribution channel workload. Also, the packaging may include but not be limited to a paper-based package, shrink wrapped package, see-through top packaging, trial-use coupons, educational materials, ancillary supplies, and/or delivery device.

"Package insert" means information accompanying the product that provides a description of how to administer the product, along with the safety and efficacy data required to allow the physician, pharmacist, and patient to make an informed decision regarding use of the product, and/or patient education information. The package insert generally is regarded as the "label" for a pharmaceutical product.

A "subject" or "patient" is a human.

"In vitro potency" as used herein is the measure of the potency or ability of a compound to activate the GLP-1 receptor in a cell-based assay. In vitro potency is expressed as the "$EC_{50}$" which is the effective concentration of compound that results in 50% activity in a single dose-response experiment. For the purposes of the present invention, in vitro potency is determined using a fluorescence assay that employs HEK-293 Aurora CRE-BLAM cells that stably express the human GLP-1 receptor. The assay is discussed in more detail on page 17 and in example 3. The in vitro potency values as disclosed herein are expressed as the $EC_{50}$ which was established by generating a dose response curve using dilutions resulting in GLP-1 compound concentrations from 3 nanomolar to 30 nanomolar. Relative in vitro potency values are established by running $Val^8$-GLP-1(7-37)OH as a control and assigning the control a reference value of 1.

The GLP-1 compounds of the present invention have sufficient homology to GLP-1(7-37)OH or a fragment of GLP-1(7-37)OH such that the compound has the ability to bind to the GLP-1 receptor and initiate a signal transduction pathway resulting in insulinotropic action or other physiological effects as described herein such as inhibition of glucagon and delay in gastric emptying. For example, GLP-1 compounds can be tested for insulinotropic activity using a cell-based assay such as that described in EP 619 322 which is a modification of the method described by Lacy, et al. (1967) *Diabetes* 16:35-39. A collagenase digest of pancreatic tissue is separated on a Ficoll gradient (27%, 23%, 20.5%, and 11% in Hank's balanced salt solution, pH 7.4). The islets are collected from the 20.5%/11% interface, washed and handpicked free of exocrine and other tissue under a stereomicroscope. The islets are incubated overnight in RPMI 1640 medium supplemented with 10% fetal bovine plasma and containing 11 mM glucose at 37° C. and 95% air/5% $CO_2$. The GLP-1 compound to be studied is prepared at a range of concentrations, preferably 3 nanomolar to 30 nanomolar in RPMI medium containing 10% fetal bovine plasma and 16.7 mM glucose. About 8 to 10 isolated islets are then transferred by pipette to a total volume of 250 µl of the GLP-1 compound containing medium in 96 well microtiter dishes. The islets are incubated in the presence of the GLP-1 compound at 37° C., 95% air, 5% $CO_2$ for 90 minutes. Then aliquots of islet-free medium are collected and 100 µl thereof are assayed for the amount of insulin present by radioimmunoassay using an Equate Insulin RIA Kit (Binax, Inc., Portland, Me.).

It is preferred that the GLP-1 compounds of the present invention have an in vitro potency no more than 10-fold lower than the in vitro potency of $Val^8$-GLP-1(7-37)OH. Preferably, the GLP-1 compounds have an in vitro potency not lower than the in vitro potency of $Val^8$-GLP-1(7-37)OH. Representative GLP-1 compounds are discussed in detail below. Furthermore, the GLP-1 compounds used in the chronic treatment regimen described herein may require modification or formulation such that blood plasma levels are maintained in the claimed efficacious range for extended time periods. Modification and formulation of GLP-1 compounds is also discussed in detail below.

Although GLP-1 has been proposed as a possible therapy for type 2 diabetes, its short half-life and susceptibility to protease degradation has made it a difficult molecule to study. Furthermore, side effects such as nausea and vomiting have been observed after a single subcutaneous or i.v. bolus administration of active GLP-1. Applicants believe this is due to the initial peak levels of the compound that are obtained immediately after administration. In order for a short acting formulation to provide a therapeutic benefit, it must be injected at a high enough dose to provide blood levels that are in the therapeutic range at least long enough to achieve a glucose lowering effect after a meal. These undesired effects occurring after administration of a relatively high dose of a short-acting GLP-1 formulation limit the amount that can be administered to patients and correspondingly limits the efficacy.

Clinical studies have established several of the physiological effects of GLP-1 which include stimulation of insulin secretion, inhibition of glucagon secretion, decrease in hepatic glucose production, inhibition of gastric emptying, and promotion of weight loss. However, GLP-1 compounds cannot be effectively used in a treatment regimen unless pharmacological levels of active GLP-1 are present continuously throughout the course of treatment. This is particularly true in order to fully exploit blood glucose lowering potential as well as other long-term physiological effects described herein.

Accordingly, the present invention describes the steady state plasma levels of an active GLP-1 compound having a specific potency necessary to achieve efficacy yet avoid or minimize side effects such as nausea and vomiting. The steady state concentration of a drug is achieved when drug elimination which is a product of clearance and concentration equals the rate of drug availability. In the context of intermittent dosage, during each interdose interval, the concentration of drug rises and falls. At steady state, the entire cycle is repeated identically in each interval. However, as discussed herein, marked fluctuations in active GLP-1 plasma concentrations between doses is responsible for side effects such as nausea and vomiting and do not result in an optimal biological response.

The treatment regimen of the present invention involves administering a GLP-1 compound such that continuous steady state plasma levels of the compound are maintained throughout a particular course of treatment for a particular condition. In the context of the present invention, "maintaining" plasma levels means that the plasma concentration of drug during the course of treatment does not fluctuate significantly once steady state levels are achieved and thus, side effects such as nausea and vomiting are avoided or minimized and at the same time an optimal therapeutic effect is obtained. Drug levels do not fluctuate significantly if they remain within the claimed efficacious range once steady state plasma levels are achieved. Surprisingly, it was discovered that the therapeutic plasma levels for exogenously administered GLP-1 compounds having a similar potency to native GLP-1 is significantly higher than levels of endogenously secreted GLP-1 in the circulation.

The present invention is based on data generated from a clinical trial wherein a long-acting GLP-1 formulation was administered via subcutaneous injection once a day at three different dose levels. After six days of dosing, drug levels reached a steady state plateau that was maintained continuously during the course of treatment. The chronic treatment regimen of the present invention may involve a GLP-1 compound administered continuously in order to obtain plasma levels within the range described herein or more preferably involves the administration of a long-acting GLP-1 compound. Long acting in the context of the present invention means that the plasma levels of an active GLP-1 compound stay within the therapeutic range described herein for at least 12 hours after delivery of a single dose. Preferably plasma levels remain within this range for at least 24 hours after delivery of a single dose. This preferred time action would result in once a day dosing.

Following administration of a sustained release formulation containing $Val^8$-GLP-1(7-37)OH on day 1, mean Cmax values of 105, 147, 300, and 222 pg/mL were achieved for doses corresponding to 2.5 mg, 3.5 mg, and two groups at 4.5 mg, respectively. These Cmax values represent the mean maximum plasma concentration of intact $Val^8$-GLP-1(7-37)OH achieved for a group of 8 patients at one of the given doses during the first day of treatment. (See FIGS. 1 and 3). The plasma concentration of $Val^8$-GLP-1(7-37)OH for all three groups resulted in some glucose lowering with levels above 200 pg/mL showing the most significant effect (Table 1). Inspection of the mean plasma profiles suggested that steady state was essentially attained after once a day dosing for 6 days and that the accumulation of drug was approximately 3-fold. On day 6, the mean Cmax values for the 2.5 mg, 3.5 mg, and 4.5 mg dosage groups were 534, 525, and 570 pg/mL, respectively. The corresponding $AUC_{(0-24)}$ values which represent exposure to the active drug were also similar: 8878, 9846, and 10619 ng*h/L, respectively. Thus, a 1.8-fold increase in dose was associated with a 1.2-fold increase in the mean steady state exposure AUC(0-24) (See FIGS. 1 and 3).

TABLE 1

| Dose (mg)/ Group | Parameter | Day 0 (Placebo) | Day 1 | Day 6 | Day 21 |
|---|---|---|---|---|---|
| 2.5/1 | $R_{max}$ (mg/dL) | 267 (17.0) | 246 (19.3) | 205 (16.3) | — |
|  | $AUC_{(0-4)}$ (mg * h/dL) | 901 (18.8) | 833 (19.2) | 654 (21.2) | — |
| 3.5/2 | $R_{max}$ (mg/dL) | 265 (15.9) | 214 (23.9) | 175 (14.7) | — |
|  | $AUC_{(0-4)}$ (mg * h/dL) | 871 (18.2) | 738 (22.2) | 557 (14.3) | — |
| 4.5/3 | $R_{max}$ (mg/dL) | 287 (22.5) | 244 (29.3) | 221 (34.9) | — |
|  | $AUC_{(0-4)}$ (mg * h/dL) | 995 (24.1) | 834 (31.5) | 704 (35.0) | — |
| 4.5/4 | $R_{max}$ (mg/dL) | 226 (15.1) | 177 (22.0) | 159 (20.2) | 156 (26.6) |
|  | $AUC_{(0-4)}$ (mg * h/dL) | 759 (14.8) | 592 (20.4) | 529 (21.0) | 516 (33.5) |

Abbreviations: $R_{max}$ = mean maximum concentration; AUC = area under the curve.

A clinically relevant fall in the pre-dose fasting blood glucose was seen after dosing in all treatment groups. The mean maximum observed glucose concentrations represented as Rmax ranged from 23% to 34% lower than the placebo controlled group on the sixth day of treatment. Furthermore, the glucose response of day 6 was similar to that seen after 21 days of treatment (See FIGS. 2 and 4). A plateau in the response was achieved at steady state concentration corresponding to the 2.5 mg and 3.5 mg doses which resulted in mean Cmax values of 534 and 525 pg/mL, respectively. Unexpectantly, no severe nausea and vomiting and only occasional, generally short episodes of nausea or vomiting was observed in groups having plasma levels below 600 pg/mL. One patient received a dose that resulted in a Cmax of 990 pg/mL of $Val^8$-GLP-1(7-37)OH and this higher level was associated with some nausea.

In addition, weight loss occurred in the treatment groups. The average amount of weight loss per patient during the 21-day dosing period was approximately 2.1 kg.

Because there will be differences in the molecular weight of GLP-1 compounds having similar potencies, the observed plasma levels for $Val^8$-GLP-1(7-37)OH are converted from pg/mL to picomolar (pmoles/L). Thus, the preferred range of plasma levels that provide maximum efficacy and yet avoid or minimize side effects such as nausea and vomiting is between about 60 and about 200 pmoles/liter for GLP-1 compounds having a potency that is similar or within two-fold the potency of $Val^8$-GLP-1(7-37)OH. More preferably, plasma levels are between about 80 picomolar and about 200 picomolar. Even more preferably, plasma levels are between about 100 picomolar and about 200 picomolar.

Thus, the invention also relates to the use of a GLP-1 compound having a potency that is similar or within two-fold the potency of $Val^8$-GLP-1(7-37)OH for the manufacture of a medicament for the normalization of blood glucose, preservation of β-cells, induction of weight loss or the treatment of a condition selected from the group consisting of: hyperglycemia, type 2 diabetes, stroke, myocardial infarction, catabolic changes that occur after surgery, obesity, and irritable bowel syndrome, wherein the medicament is adapted for chronic administration such that chronic steady state plasma levels of the GLP-1 compound are maintained between about 60 picomolar and about 200 picomolar, preferably between about 80 picomolar and about 200 picomolar, more preferably between about 100 picomolar and about 200 picomolar Plasma levels as discussed herein refer to the concentration of an active GLP-1 compound as measured in blood plasma. Plasma contains an enzyme known as DPP-IV which readily cleaves amino acids at the N-terminus of GLP-1 compounds. It is known that GLP-1 must have an intact Histidine at the N-terminus to be active. For example GLP-1(7-37)OH is rapidly degraded to GLP-1(9-37)OH once it is released into the plasma. GLP-1(9-37)OH is not active. Furthermore, GLP-1 can also be inactivated by cleavage at the C-terminus. An inactive GLP-1(7-33) metabolite has also been reported in the literature. The plasma levels described herein for $Val^8$-GLP-1(7-37)OH were measured using a sandwich radioimmunoassay. The assay makes use of an antibody that specifically recognizes the intact amino-terminus of $Val^8$-GLP-1(7-37)OH in combination with another antibody which recognizes the intact C-terminus of $Val^8$-GLP-1(7-37)OH. Thus, only plasma levels of active $Val^8$-GLP-1(7-37)OH are measured. (See Example 2).

Plasma levels of active GLP-1 compounds other than $Val^8$-GLP-1(7-37)OH can similarly be measured by generating antibodies by methods well-known in the art that specifically identify the intact N-terminus of the compound being tested and do not cross-react with native GLP-1.

Some GLP-1 derivatives such as $Arg^{34}Lys^{26}$-(N-ε-(γ-Glu (N-α-hexadecanoyl)))-GLP-1(7-37) are long-acting because they bind to plasma albumin and slowly dissociate from albumin and are released into the plasma as unbound derivatives that can bind the GLP-1 receptor and initiate a signal. For the purposes of the present invention, plasma levels refer to the concentration of active GLP-1 derivatives such as Arg$^{34}$Lys$^{26}$-(N-ε-(γ-Glu(N-α-hexadecanoyl)))-GLP-1(7-37) that are present in the plasma not bound to albumin.

To achieve maximum efficacy while minimizing side effects, the plasma levels of a GLP-1 compound should not fluctuate significantly once steady state levels are obtained during the course of treatment. Levels do not fluctuate significantly if they are maintained within the ranges described herein once steady state levels are achieved throughout a course of treatment. Most preferably, plasma levels of a GLP-1 compound with a potency similar to or within two-fold that of Val$^8$-GLP-1(7-37)OH are maintained between about 100 picomolar and about 200 picomolar throughout a course of treatment once steady state levels are obtained. For example, FIG. 3 depicts plasma levels of Val$^8$-GLP-1(7-37)OH which remain flat and do not fluctuate significantly over the course of 15 days based on once a day dosing. Levels are maintained between about 400 and about 600 pg/mL which corresponds to between about 120 picomolar and 180 picomolar.

The optimal range of plasma levels appropriate for Val$^8$-GLP-1(7-37)OH and GLP-1 compounds of similar potency (See Table 2) can also be applied to other GLP-1 compounds including Exendin-3 and Exendin-4 which have different potencies. GLP-1 compounds of similar potency include compounds that have within two-fold the activity of Val$^8$-GLP-1(7-37)OH as measured by an in vitro potency assay.

The preferred assay for the purposes of the present invention measures EC$_{50}$ potency using HEK-293 Aurora CRE-BLAM cells that stably express the human GLP-1 receptor. These HEK-293 cells have stably integrated a DNA vector having a cAMP response element (CRE) driving expression of the β-lactamase (BLAM) gene. The interaction of a GLP-1 agonist with the receptor initiates a signal that results in activation of the cAMP response element and subsequent expression of β-lactamase. The β-lactamase CCF2/AM substrate that emits flourescence when it is cleaved by β-lactamase (Aurora Biosciences Corp.) can then be added to cells that have been exposed to a specific amount of GLP-1 agonist to provide a measure of GLP-1 agonist potency. The assay is further described in Zlokarnik, et al. (1998) *Science* 279:84-88 (See also Example 3). The EC$_{50}$ values listed in Table 2 were determined using the BLAM assay described above by generating a dose response curve using dilutions from 3 nanomolar to 30 nanomolar.

Exendin-4 has a potency that is approximately 5-fold higher than Val$^8$-GLP-1(7-37)OH; thus, optimum plasma levels of Exendin-4 will be approximately 5-fold lower than the levels appropriate for Val$^8$-GLP-1(7-37)OH and compounds of similar potency. This would correspond to plasma levels in the range between about 6 picomolar and about 40 picomolar, preferably between about 12 picomolar and about 30 picomolar. Another example of a GLP-1 compound with increased potency is Val$^8$-Glu$^{22}$-GLP-1(7-37)OH which has a potency approximately 3-fold higher than Val$^8$-GLP-1(7-37)OH. Thus, optimum plasma levels of this compound will be approximately 3-fold lower than the levels determined for. Val$^8$-GLP-1 (7-37) OH.

TABLE 2

| GLP-1 Compound | In vitro activity relative to Val$^8$-GLP-1(7-37)OH |
|---|---|
| Val$^8$-GLP-1(7-37)OH | 1 |
| Val$^8$-GLP-1(7-36)NH$_2$ | 1.06 |
| GLP-1(7-37)OH | 2.06 |
| GLP-1(7-36)NH$_2$ | 1.50 |
| Gly$^8$-GLP-1(7-37)OH | 1.67 |
| Val$^8$-Tyr$^{12}$-GLP-1(7-37)OH | 1.73 |
| Val$^8$-Trp$^{12}$-GLP-1(7-37)OH | 1.07 |
| Val$^8$-Leu$^{16}$-GLP-1(7-37)OH | 1.13 |
| Val$^8$-Lys$^{22}$-GLP-1(7-37)OH | 1.22 |
| Exendin-4 | 4.5 |
| Val$^8$-Glu$^{22}$-GLP-1(7-37)OH | 3.33 |
| Val$^8$-Arg$^{26}$-GLP-1(7-37)OH | 1.47 |
| Val$^8$-Ala$^{27}$-GLP-1(7-37)OH | 1 |
| Arg$^{34}$Lys$^{26}$-(N-ε-(γ-Glu(N-α-hexadecanoyl)))-GLP-1(7-37) | 1.92 |

Thus, the range of plasma levels appropriate for a GLP-1 compound with a potency that differs from that of Val$^8$-GLP-1(7-37)OH can be determined. For example, a range of plasma levels for a particular GLP-1 compound is between about 60/X and 200/X, preferably between about 60/X and 150/X, most preferably between about 100/X and about 150/X wherein X is the in vitro potency of the GLP-1 compound relative to Val$^8$-GLP-1(7-37)OH wherein Val$^8$-GLP-1(7-37)OH has a reference value of 1.

Further, the invention relates to the use of a GLP-1 compound for the manufacture of a medicament for the normalization of blood glucose, preservation of β-cells, induction of weight loss, or the treatment of a condition selected from the group consisting of: hyperglycemia, type 2 diabetes, stroke, myocardial infarction, catabolic changes that occur after surgery, obesity, and irritable bowel syndrome, wherein the medicament is adapted for chronic administration such that chronic plasma levels of the GLP-1 compound are maintained between about 60/X picomolar and about 200/X picomolar wherein X is the in vitro potency of the GLP-1 compound relative to Val$^8$-GLP-1(7-37)OH which has a reference value of 1.

Maintaining plasma levels within the range discovered by the inventors of the present invention provides numerous clinical benefits as well as benefits from a patient convenience standpoint. There is little or no risk of hypoglycemia to the subject when using this treatment regimen. Additionally, this regimen minimizes invasive, planning, and/or time-consuming events. Furthermore, the regimen provides convenience to the patient by reducing blood glucose self-monitoring in conjunction with use. Most preferably, blood glucose self-monitoring is reduced significantly or eliminated for subjects using this treatment regimen. For example, this use does not require patient planning before, during, or following a meal. Most preferably, subjects do not need to link use of this regimen with any glucose, calorie, or sustenance consumption event of any quantity. Furthermore, use of this invention preferably limits any dose titration needed for a subject to determine the effective amount required. Most preferably, no dose titration is required thereby making one or two doses appropriate for all patients.

While pre-clinical data has alluded to some of the long-term health benefits associated with GLP-1 therapy, it has not been possible to take advantage of these long-term benefits in human patients due to the lack of understanding regarding the steady plasma levels required to achieve such benefits.

Maintaining plasma levels of intact GLP-1 compounds as described herein induce long-term benefits derived from the suppression of glucagon, upregulation of somatostatin, stimulation of insulin gene transcription, up-regulation of IDX-1/PDX-1 or other growth factors, improvement of β cell function, activation of dormant β cells, differentiation of cells into β cells, β cell replication, and β cell proliferation. For the purposes of the present invention, a method of preserving β cells may be due to all or some or one of the following effects: improvement of β cell function, activation of dormant β cells, differentiation of cells into β cells, β cell replication, preventing β-cell deterioration such as by inhibition of apoptosis, and β cell proliferation.

Maintaining plasma levels of intact GLP-1 compounds as described herein induce long-term benefits such as appetite suppression resulting in weight loss or lack of weight gain. For example, obesity and related conditions are treated or prevented by this chronic treatment regimen. Any and all reduction in weight via less weight gain, no weight gain, and/or weight loss provides the subject with overall positive physical and psychological health effects, contributes to lessening risk factors linked to excessive body weight, and enforces compliant use of the compounds thereby reducing potential blood glucose excursions and its concomitant effects.

Another benefit of chronic exposure to GLP-1 compounds within the range of claimed serum levels includes the elimination of the delay on gastric emptying that occurs when GLP-1 compounds are first administered. By analyzing the timing of glucose peaks relative to the ingestion of a meal for patients receiving a GLP-1 compound, it was determined that the delay in gastric emptying caused by the presence of a GLP-1 compound is approximately 2 to 3 hours. Surprisingly, after 6 days of chronic GLP-1 compound therapy, the analysis of glucose peaks indicated that this delay in gastric emptying was eliminated. Thus, chronic exposure to GLP-1 compounds within the claimed serum level range leads to an elimination of GI effects such as a delay in gastric emptying and, therefore, increases patient tolerability to the drug and potentially minimizes side effects.

This chronic treatment regimen may include treatment using GLP-1 compounds along with other blood glucose lowering drugs such as metformin, sulfonyl ureas, thiazolidinediones, and/or bisguanidines. The range of plasma levels described herein is appropriate when GLP-1 compounds are used as a monotherapy or used in conjunction with oral anti-diabetic agents.

The term "GLP-1 compounds" refers to GLP-1(7-37)OH and GLP-1(7-36)NH$_2$ and analogs and derivatives thereof. GLP-1 compounds also include Exendin-3 and Exendin-4 and analogs and derivatives thereof. Any of these GLP-1 compounds may need further modification or be formulated such that blood plasma levels are maintained for extended time periods following a single dose. GLP-1 peptides can be made by a variety of methods known in the art such as solid-phase synthetic chemistry, purification of GLP-1 molecules from natural sources, recombinant DNA technology, or a combination of these methods. For example, methods for preparing GLP-1 peptides are described in U.S. Pat. Nos. 5,118,666, 5,120,712, 5,512,549, 5,977,071, and 6,191,102. As is the custom in the art, the N-terminal residue of a GLP-1 compound is represented as position 7.

The two naturally occurring truncated GLP-1 peptides are represented in formula I, SEQ ID NO: 1.

```
                                    Formula I, SEQ ID NO:1
  7   8   9  10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Xaa
``` wherein:

Xaa at position 37 is Gly, or —NH$_2$.

Preferably, a GLP-1 compound has the amino acid sequence of SEQ ID NO. 1 or is modified so that from one, two, three, four or five amino acids differ from SEQ ID NO: 1.

Some GLP-1 compounds known in the art include, for example, GLP-1(7-34) and GLP-1(7-35), GLP-1(7-36), Gln$^9$-GLP-1(7-37), D-Gln$^9$-GLP-1(7-37), Thr$^{16}$-Lys$^{18}$-GLP-1(7-37), and Lys$^{18}$-GLP-1(7-37). GLP-1 compounds such as GLP-1(7-34) and GLP-1(7-35) are disclosed in U.S. Pat. No. 5,118,666, herein incorporated by reference. Other known biologically active GLP-1 analogs are disclosed in U.S. Pat. Nos. 5,977,071; 5,545,618; 5,705,483; 5,977,071; 6,133,235: and Adelhorst, et al., *J. Biol. Chem.* 269:6275 (1994).

GLP-1 compounds also include polypeptides in which one or more amino acids have been added to the N-terminus and/or C-terminus of GLP-1(7-37)OH, or fragments or analogs thereof. Preferably from one to six amino acids are added to the N-terminus and/or from one to eight amino acids are added to the C-terminus of GLP-1(7-37)OH. It is preferred that GLP-1 compounds of this type have up to about thirty-nine amino acids. The amino acids in the "extended" GLP-1 compounds are denoted by the same number as the corresponding amino acid in GLP-1(7-37)OH. For example, the N-terminal amino acid of a GLP-1 compound obtained by adding two amino acids to the N-terminus of GLP-1(7-37)OH is at position 5; and the C-terminal amino acid of a GLP-1 compound obtained by adding one amino acid to the C-terminus of GLP-1(7-37)OH is at position 39. Amino acids 1-6 of an extended GLP-1 compound are preferably the same as or a conservative substitution of the amino acid at the corresponding position of GLP-1(1-37)OH. Amino acids 38-45 of an extended GLP-1 compound are preferably the same as or a conservative substitution of the amino acid at the corresponding position of Exendin-3 or Exendin-4. The amino acid sequence of Exendin-3 and Exendin-4 are represented in formula II, SEQ ID NO: 2.

```
                                           SEQ ID NO: 2
  7   8   9  10  12  12  13  14  15  16  17
His-Xaa-Xaa-Gly-Thr-Phe-Thr-Ser-Asp-Leu-Ser 18  19  20  21  22  23  24  25  26  27  28
Lys-Gln-Met-Glu-Glu-Glu-Ala-Val-Arg-Leu-Phe- 29  30  31  32  33  34  35  36  37  38  39
Ile-Glu-Trp-Leu-Lys-Asn-Gly-Gly-Pro-Ser-Ser- 40  41  42  43  44  45
Gly-Ala-Pro-Pro-Pro-Ser
``` wherein:

Xaa at position 8 is Ser or Gly; and

Xaa at position 9 is Asp or Glu;

As used herein, a conservative substitution is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape.

A preferred group of GLP-1 compounds is comprised of GLP-1 analogs of formula III (SEQ ID NO: 3):

```
                       Formula III (SEQ ID NO: 3)
 7   8   9  10  11  12  13  14  15  16  17
Xaa-Xaa-Xaa-Gly-Xaa-Xaa-Thr-Xaa-Asp-Xaa-Xaa- 18  19  20  21  22  23  24  25  26  27  28
Xaa-Xaa-Xaa-Xaa-Xaa-Xaa-Xaa-Xaa-Xaa-Xaa-Phe- 29  30  31  32  33  34  35  36  37  38  39
Ile-Xaa-Xaa-Xaa-Xaa-Xaa-Xaa-Xaa-Xaa-Xaa-Xaa- 40  41  42  43  44  45
Xaa-Xaa-Xaa-Xaa-Xaa-Xaa
``` wherein:

Xaa at position 7 is: L-histidine, D-histidine, desamino-histidine, 2-amino-histidine, β-hydroxy-histidine, homo-histidine, α-fluoromethyl-histidine or α-methyl-histidine;

Xaa at position 8 is Ala, Gly, Ser, Thr, Leu, Ile, Val, Glu, Asp, or Lys;

Xaa at position 9 is Glu, Asp, Lys, Thr, Ser, Arg, Trp, Phe, Tyr, or His;

Xaa at position 11 is Thr, Ala, Gly, Ser, Leu, Ile, Val, Glu, Asp, Arg, His, or Lys;

Xaa at position 14 is Ser, Ala, Gly, Thr, Leu, Ile, Val, Glu, Asp, or Lys;

Xaa at position 12 is His, Trp, Phe, or Tyr

Xaa at position 16 is Val, Ala, Gly, Ser, Thr, Leu, Ile, Tyr, Glu, Asp, Trp, His, Phe, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, His, Pro, Arg, or Lys;

Xaa at position 19 is Tyr, Phe, Trp, Glu, Asp, Gly, Gln, Asn, Arg, Cys, or Lys;

Xaa at position 20 is Leu, Ala, Gly, Ser, Thr, Ile, Val, Glu, Asp, Met, or Lys;

Xaa at position 21 is Glu, Asp, or Lys;

Xaa at position 22 is Gly, Ala, Ser, Thr, Leu, Ile, Val, Glu, Asp, or Lys;

Xaa at position 23 is Gln, Asn, Arg, Glu, Asp, His, or Lys;

Xaa at position 24 is Ala, Gly, Ser, Thr, Leu, Ile, Val, Arg, Glu, Asp, or Lys;

Xaa at position 25 is Ala, Gly, Ser, Thr, Leu, Ile, Val, Glu, Asp, or Lys;

Xaa at position 26 is Lys, Arg, Gln, Glu, Asp, Trp, Tyr, Phe, or His;

Xaa at position 27 is Glu, Asp, Ala, His, Phe, Tyr, Trp, Arg, Leu, or Lys;

Xaa at position 30 is Ala, Gly, Ser, Thr, Leu, Ile, Val, Glu, Asp, His, or Lys;

Xaa at position 31 is Trp, Phe, Tyr, Glu, Asp, Ser, Thr, Arg, or Lys;

Xaa at position 32 is Leu, Gly, Ala, Ser, Thr, Ile, Val, Glu, Asp, or Lys;

-continued

Xaa at position 33 is Val, Gly, Ala, Ser, Thr, Leu, Ile, Glu, Asp, Arg, or Lys;

Xaa at position 34 is Lys, Arg, Glu, Asp, Asn, or His;

Xaa at position 35 is Gly, Ala, Ser, Thr, Leu, Ile, Val, Glu, Asp, Arg, Trp, Tyr, Phe, Pro, His, or Lys;

Xaa at position 36 is Arg, Lys, Glu, Asp, Thr, Ser, Trp, Tyr, Phe, Gly, or His;

Xaa at position 37 is Gly, Ala, Ser, Thr, Leu, Ile, Val, Glu, Asp, His, Lys, Arg, Trp, Tyr, Phe, Gly-Pro, Gly-Pro-NH$_2$, —NH$_2$ or is deleted;

Xaa at position 38 is Arg, Lys, Glu, Asp, Ser, or His, or is deleted;

Xaa at position 39 is Arg, Lys, Glu, Asp, Ser, or His, or is deleted;

Xaa at position 40 is Asp, Glu, Gly, or Lys, or is deleted;

Xaa at position 41 is Phe, Trp, Tyr, Glu, Asp, Ala, or Lys, or is deleted;

Xaa at position 42 is Pro, Lye, Glu, or Asp, or is deleted;

Xaa at position 43 is Glu, Asp, Pro, or Lys, or is deleted;

Xaa at position 44 is Glu, Asp, Pro, or Lys, or is deleted; and

Xaa at position 45 is Val, Glu, Asp, Ser, or Lys, or is deleted, or a C-1-6-ester, or amide, or C-1-6-alkylamide, or C-1-6-dialkylamide thereof; provided that when the amino acid at position 37, 38, 39, 40, 41, 42, 43, or 44 is deleted, then each amino acid downstream of that amino acid is also deleted. It is preferred that the analogs encompassed by formula III, have not more than six amino acids that differ from the corresponding amino acids in GLP-1(7-37)OH, GLP-1(7-36)NH$_2$, Exendin-3, or Exendin-4. It is more preferred that the analogs encompassed by formula III have between one and five amino acids that differ from the corresponding amino acids in GLP-1(7-37)OH, GLP-1(7-36)NH$_2$, Exendin-3, or Exendin-4.

Another preferred group of GLP-1 compounds is comprised of GLP-1 analogs of formula IV (SEQ ID NO: 4):

formula IV (SEQ ID NO: 4)
His-Xaa$_8$-Glu-Gly-Xaa$_{11}$-Xaa$_{12}$-Thr-Ser-Asp-Xaa$_{16}$-Ser-
Ser-Tyr-Leu-Glu-Xaa$_{22}$-Xaa$_{23}$-Xaa$_{24}$-Ala-Xaa$_{26}$-Xaa$_{27}$-Phe-
Ile-Ala-Xaa$_{31}$-Leu-Xaa$_{33}$-Xaa$_{34}$-Xaa$_{35}$-Xaa$_{36}$-R wherein:
Xaa$_8$ is: Gly, Ala, Val, Leu, Ile, Ser, or Thr;

Xaa$_{11}$ is: Asp, Glu, Arg, Thr, Ala, Lys, or His; Xaa$_{12}$ is: His, Trp, Phe, or Tyr;

Xaa$_{16}$ is: Leu, Ser, Thr, Trp, His, Phe, Asp, Val, Glu, or Ala;

Xaa$_{22}$ is: Gly, Asp, Glu, Gln, Asn, Lys, Arg, Cys, or Cysteic Acid;

Xaa$_{23}$ is: His, Asp, Lys, Glu, or Gln;

Xaa$_{24}$ is: Glu, His, Ala, or Lys;

Xaa$_{26}$ is: Asp, Lys, Glu, or His;

Xaa$_{27}$ is: Ala, Glu, His, Phe, Tyr, Trp, Arg, or Lys;

Xaa$_{30}$ is: Ala, Glu, Asp, Ser, or His;

Xaa$_{33}$ is: Asp, Arg, Val, Lys, Ala, Gly, or Glu;

Xaa$_{34}$ is: Glu, Lys, or Asp;

-continued

Xaa₃₅ is: Thr, Ser, Lys, Arg, Trp, Tyr, Phe, Asp, Gly, Pro, His, or Glu;

Xaa₃₆ is: Arg, Glu, or His;
R is: Lys, Arg, Thr, Ser, Glu, Asp, Trp, Tyr, Phe, His, —NH₂, Gly, Gly-Pro, or Gly-Pro-NH₂,

It is preferred that the analogs encompassed by formula IV, have not more than six amino acids that differ from the corresponding amino acids in GLP-1(7-37)OH, or GLP-1(7-36)NH₂. It is more preferred that the analogs encompassed by formula IV have between one and five amino acids that differ from the corresponding amino acids in GLP-1(7-37)OH, or GLP-1(7-36)NH₂.

Another preferred group of GLP-1 compounds is comprised of GLP-1 analogs of formula V (SEQ ID NO: 5):

formula III (SEQ ID NO: 5)
His-Xaa₈-Glu-Gly-Thr-Xaa₁₂-Thr-Ser-Asp-Xaa₁₆-Ser-
Ser-Tyr-Leu-Glu-Xaa₂₂-Xaa₂₃-Ala-Ala-Xaa₂₆-Glu-Phe-
Ile-Xaa₃₀-Trp-Leu-Val-Lys-Xaa₃₅-Arg-R wherein:
Xaa₈ is: Gly, Ala, Val, Leu, Ile, Ser, or Thr;

Xaa₁₂ is: His, Trp, Phe, or Tyr;

Xaa₁₆ is: Leu, Ser, Thr, Trp, His, Phe, Asp, Val, Glu,
or Ala;

Xaa₂₂ is: Gly, Asp, Glu, Gln, Asn, Lys, Arg, Cys,
or Cysteic Acid;

Xaa₂₃ is: His, Asp, Lys, Glu, or Gln;

Xaa₂₆ is: Asp, Lys, Glu, or His;

Xaa₃₀ is: Ala, Glu, Asp, Ser, or His;

Xaa₃₅ is: Thr, Ser, Lys, Arg, Trp, Tyr, Phe, Asp, Gly,
Pro, His, or Glu;
R is: Lys, Arg, Thr, Ser, Glu, Asp, Trp, Tyr, Phe, His,
—NH₂, Gly, Gly-Pro, or Gly-Pro-NH₂, or is deleted.

It is preferred that the analogs encompassed by formula V, have not more than six amino acids that differ from the corresponding amino acids in GLP-1(7-37)OH, or GLP-1(7-36)NH₂. It is more preferred that the analogs encompassed by formula V have between one and five amino acids that differ from the corresponding amino acids in GLP-1(7-37)OH or GLP-1(7-36)NH₂.

Another preferred group of GLP-1 compounds is comprised of GLP-1 analogs of formula VI (SEQ ID NO: 6):

formula VI (SEQ ID NO: 6)
His-Xaa₈-Glu-Gly-Thr-Phe-Thr-Ser-Asp-Val-Ser-Ser-
Tyr-Leu-Glu-Xaa₂₂-Xaa₂₃-Ala-Ala-Lys-Xaa₂₇-Phe-Ile-
Xaa₃₀-Trp-Leu-Val-Lys-Gly-Arg-R wherein:
Xaa₈ is: Gly, Ala, Val, Leu, Ile, Ser, or Thr;

Xaa₂₂ is: Gly, Asp, Glu, Gln, Asn, Lys, Arg, Cys,
or Cysteic Acid;

Xaa₂₃ is: His, Asp, Lys, Glu, or Gln;

Xaa₂₇ is: Ala, Glu, His, Phe, Tyr, Trp, Arg, or Lys

Xaa₃₀ is: Ala, Glu, Asp, Ser, or His;
R is: Lys, Arg, Thr, Ser, Glu, Asp, Trp, Tyr, Phe, His,
—NH₂, Gly, Gly-Pro, or Gly-Pro-NH₂, or is deleted.

Another preferred group of GLP-1 compounds is comprised of GLP-1 analogs of formula VII (SEQ ID NO. 7):

(SEQ ID NO: 7)
Xaa$_7$-Xaa$_8$-Glu-Gly-Thr-Phe-Thr-Ser-Asp-Val-Ser-
Ser-Tyr-Leu-Glu-Xaa$_{22}$-Gln-Ala-Ala-Lys-Glu-Phe-
Ile-Ala-Trp-Leu-Val-Lys-Gly-Arg-R wherein:

Xaa$_7$ is L-histidine, D-histidine, desamino-histidine, 2amino-histidine, β-hydroxy-histidine, homohistidine, α-fluoromethyl-histidine or α-methyl-histidine;

Xaa$_8$ is glycine, alanine, valine, leucine, isoleucine, serine or threonine. Preferably, Xaa$_8$ is glycine, valine, leucine, isoleucine, serine or threonine;

Xaa$_{22}$ is aspartic acid, glutamic acid, glutamine, asparagine, lysine, arginine, cysteine, or cysteic acid.

R is —NH$_2$ or Gly(OH).

Most preferred GLP-1 compounds of formula I, II, III, IV, V, and VI comprise GLP-1 analogs wherein the backbone for such analogs or fragments contains an amino acid other than alanine at position 8 (position 8 analogs). Preferred amino acids at position 8 are glycine, valine, leucine, isoleucine, serine, threonine, or methionine and more preferably are valine or glycine.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 30 is glutamic acid, aspartic acid, serine, or histidine and more preferably glutamic acid.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 37 is histidine, lysine, arginine, threonine, serine, glutamic acid, aspartic acid, tryptophan, tyrosine, phenylalanine and more preferably histidine.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 23 is lysine, arginine, glutamic acid, aspartic acid, and histidine and more preferably lysine or glutamic acid.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 27 is alanine, lysine, arginine, tryptophan, tyrosine, phenylalanine, or histidine and more preferably alanine.

In the nomenclature used herein to describe GLP-1 compounds, the substituting amino acid and its position is indicated prior to the parent structure. For example Val$^8$-GLP-1(7-37)OH designates a GLP-1 compound in which the alanine normally found at position 8 in GLP-1(7-37)OH (formula I, SEQ ID NO:1) is replaced with valine.

Other preferred GLP-1 compounds include: Val$^8$-GLP-1(7-37)OH, Gly$^8$-GLP-1(7-37)OH, Glu$^{22}$-GLP-1(7-37)OH, Asp$^{22}$-GLP-1(7-37)OH, Arg$^{22}$-GLP-1(7-37)OH, Lys$^{22}$-GLP-1(7-37)OH, Cys$^{22}$-GLP-1(7-37)OH, Val$^8$-Glu$^{22}$-GLP-1(7-37)OH, Val$^8$-Asp$^{22}$-GLP-1(7-37)OH, Val$^8$-Arg$^{22}$-GLP-1(7-37)OH, Val$^8$-Lys$^{22}$-GLP-1(7-37)OH, Val$^8$-Cys$^{22}$-GLP-1(7-37)OH, Gly$^8$-Glu$^{22}$-GLP-1(7-37)OH, Gly$^8$-Asp$^{22}$-GLP-1(7-37)OH, Gly$^8$-Arg$^{22}$-GLP-1(7-37)OH, Gly$^8$-Lys$^{22}$-GLP-1(7-37)OH, Gly$^8$-Cya$^{22}$-GLP-1(7-37)OH, Glu$^{22}$-GLP-1(7-36)NH$_2$, Asp$^{22}$-GLP-1(7-36)NH$_2$, Arg$^{22}$-GLP-1(7-36)NH$_2$, Lys$^{22}$-GLP-1(7-36)NH$_2$, Cys$^{22}$-GLP-1(7-36)NH$_2$, Val$^8$-Glu$^{22}$-GLP-1(7-36)NH$_2$, Val$^8$-Asp$^{22}$-GLP-1(7-36)NH$_2$, Val$^8$-Arg$^{22}$-GLP-1(7-36)NH$_2$, Val$^8$-Lys$^{22}$-GLP-1(7-36)NH$_2$, Val$^8$-Cys$^{22}$-GLP-1(7-36)NH$_2$, GLY$^8$-Glu$^{22}$-GLP-1(7-36)NH$_2$, Gly$^8$-Asp$^{22}$-GLP-1(7-36)NH$_2$, Gly$^8$-Arg$^{22}$-GLP-1(7-36)NH$_2$, Gly$^8$-Lys$^{22}$-GLP-1(7-36)NH$_2$, Gly$^8$-Cys$^{22}$-GLP-1(7-36)NH$_2$, Lys$^{23}$-GLP-1(7-37)OH, Val$^8$-Lys$^{23}$-GLP-1(7-37)OH, Gly$^8$-Lys$^{23}$-GLP-1(7-37)OH, His$^{24}$-GLP-1(7-37)OH, Val$^8$-His$^{24}$-GLP-1(7-37)OH, Gly$^8$-His$^{24}$-GLP-1(7-37)OH, Lys$^{24}$-GLP-1(7-37)OH, Val$^8$-Lys$^{24}$-GLP-1(7-37)OH, Gly$^8$-Lys$^{23}$-GLP-1(7-37)OH, Glu$^{30}$-GLP-1(7-37)OH, Val$^8$-Glu$^{30}$-GLP-1(7-37)OH, Gly$^8$-Glu$^{30}$-GLP-1(7-37)OH, Asp$^{30}$-GLP-1(7-37)OH, Val$^8$-Asp$^{30}$-GLP-1(7-37)OH, Gly$^8$-Asp$^{30}$-GLP-1(7-37)OH, Gln$^{30}$-GLP-1(7-37)OH, Val$^8$-Gln$^{30}$-GLP-1(7-37)OH, Gly$^8$-Gln$^{30}$-GLP-1(7-37)OH, Tyr$^{30}$-GLP-1(7-37)OH, Val$^8$-Tyr$^{30}$-GLP-1(7-37)OH, Gly$^8$-Tyr$^{30}$-GLP-1(7-37)OH, Ser$^{30}$-GLP-1(7-37)OH, Val$^8$-Ser$^{30}$-GLP-1(7-37)OH, Gly$^8$-Ser$^{30}$-GLP-1(7-37)OH, His$^{30}$-GLP-1(7-37)OH, Val$^8$-His$^{30}$-GLP-1(7-37)OH, Gly$^8$-His$^{30}$-GLP-1(7-37)OH, Glu$^{34}$-GLP-1(7-37)OH, Val$^8$-Glu$^{34}$-GLP-1(7-37)OH, Gly$^8$-Glu$^{34}$-GLP-1(7-37)OH, Ala$^{34}$-GLP-1(7-37)OH, Val$^8$-Ala$^{34}$-GLP-1(7-37)OH, Gly$^8$-Ala$^{34}$-GLP-1(7-37)OH, Gly$^{34}$-GLP-1(7-37)OH, Val$^8$-Gly$^{34}$-GLP-1(7-37)OH, Gly$^8$-Gly$^{34}$-GLP-1(7-37)OH, Ala$^{35}$-GLP-1(7-37)OH, Val$^8$-Ala$^{35}$-GLP-1(7-37)OH, Gly$^8$-Ala$^{35}$-GLP-1(7-37)OH, Lys$^{35}$-GLP-1(7-37)OH, Val$^8$-Lys$^{35}$-GLP-1(7-37)OH, Gly$^8$-Lys$^{35}$-GLP-1(7-37)OH, His$^{35}$-GLP-1(7-37)OH Val$^8$-His$^{35}$-GLP-1(7-37)OH, Gly$^8$-His$^{35}$-GLP-1(7-37)OH, Pro$^{35}$-GLP-1(7-37)OH, Val$^8$-Pro$^{35}$-GLP-1(7-37)OH, Gly$^8$-Pro$^{35}$-GLP-1(7-37)OH, Glu$^{35}$-GLP-1(7-37)OH Val$^8$-Glu$^{35}$-GLP-1(7-37)OH, Gly$^8$-Glu$^{35}$-GLP-1(7-37)OH, Val$^8$-Ala$^{27}$-GLP-1(7-37)OH, Val$^8$-His$^{37}$-GLP-1(7-37)OH, Val$^8$-Glu$^{22}$-Lys$^{23}$-GLP-1(7-37)OH, Val$^8$-Glu$^{22}$-Glu$^{23}$-GLP-1(7-37)OH, Val$^8$-Glu$^{22}$-Ala$^{27}$-GLP-1(7-37)OH, Val$^8$-Gly$^{34}$-Lys$^{35}$-GLP-1(7-37)OH, Val$^8$-His$^{37}$-GLP-1(7-37)OH, and Gly$^8$-His$^{37}$-GLP-1(7-37)OH.

More preferred GLP-1 compounds are Val$^8$-GLP-1(7-37)OH, Gly$^8$-GLP-1(7-37)OH, Glu$^{22}$-GLP-1(7-37)OH, Lys$^{22}$-GLP-1(7-37)OH, Val$^8$-Glu$^{22}$-GLP-1(7-37)OH, Val$^8$-Lys$^{22}$-GLP-1(7-37)OH, Gly$^8$-Glu$^{22}$-GLP-1(7-37)OH, Gly$^8$-Lys$^{22}$-GLP-1(7-37)OH, Glu$^{22}$-GLP-1(7-36)NH$_2$, Lys$^{22}$-GLP-1(7-36)NH$_2$, Val$^8$-Glu$^{22}$-GLP-1(7-36)NH$_2$, Val$^8$-Lys$^{22}$-GLP-1(7-36)NH$_2$, Gly$^8$-Glu$^{22}$-GLP-1(7-36)NH$_2$, Gly$^8$-Lys$^{22}$-GLP-1(7-36)NH$_2$, Val$^8$-His$^{37}$-GLP-1(7-37)OH, Gly$^8$-His$^{37}$-GLP-1(7-37)OH, Arg$^{34}$-GLP-1(7-36)NH$_2$, and Arg$^{34}$-GLP-1(7-37)OH.

A GLP-1 compound also includes a "GLP-1 derivative" which is defined as a molecule having the amino acid sequence of GLP-1 or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties.

The GLP-1 compound used for the chronic treatment regimen may require modification or formulation so that blood plasma levels are maintained in the claimed efficacious range for extended time periods. Various means can be employed to achieve a protracted time action including, for example, the incorporation of GLP-1 compounds into suspended amorphous or crystalline particles wherein the GLP-1 compound is complexed with zinc or protamine and slowly solubilizes upon administration. Another means includes derivatizing a GLP-1 compound such that it binds plasma albumin and slowly dissociates over time. In addition, depot formulations wherein an bioadsorbable polymer is used to provide sustained release over time are also suitable for use in the present invention.

For example, GLP-1 compound can be incorporated into zinc crystals which have a protracted time action by dissolving the selected GLP-1 peptide in a glycine-free solution at a pH of about 9.5 to about 11.5. This "alkaline normalization" step appears to reduce the content of β-sheet conformation in the peptide and enhance the α-helix conformation that is important for solubility and bioavailability of some GLP-1 compounds. This step also serves to maintain the peptide in a preferred α-helix conformation prior to the subsequent process step. This key step thus "normalizes" variation in bulk lots of the peptide into a more reproducible, homogenous solution.

Preferably, the peptide concentration in the alkaline normalization solution is greater than 5 mg/mL. More preferably, the concentration is about 10 mg/mL to about 30 mg/mL. Other ranges of preferred concentration of dissolved peptide are about 5 mg/mL to about 25 mg/mL, about 8 mg/mL to about 25 mg/mL and about 10 mg/mL to about 20 mg/mL. The most preferred concentration is about 15 mg/mL.

Preferably, an aqueous alkaline solution comprising only water and a base such as NaOH, KOH or ammonium hydroxide is employed to dissolve the peptide. A more preferred base is NaOH.

Preferably, the pH of the alkaline normalization step is about 10.0 to about 11.0. More preferably, the pH is about 10.5. The alkaline solution comprising the dissolved peptide may be allowed to sit quiescently for a period of about 5 minutes to about 3 hours at ambient temperature, which, although it is not to be construed as a limitation, is generally between about 20° C. and about 25° C. The alkaline solution may also be gently stirred. More preferably, the dissolved alkaline peptide solution will sit quiescently for about 1 hour at ambient temperature. One skilled in the art will recognize that combinations of pH, time, temperature and stirring conditions for this step can be readily established for each peptide that ensures "normalization" of the peptide conformation is complete yet avoids or minimizes chemical degradation that may occur to the peptide.

The next step in the process for preparing crystals of a selected peptide is the addition of glycine. Amino acids such as glycine bind zinc ions which also bind very tightly to the histidine residue(s) in a peptide. Thus, competition for zinc binding may play a role in the formation of peptide crystals, as well as in the stability of subsequent crystalline compositions. The glycine added to the alkaline peptide solution may be in a solid form or in a stock solution. Preferably, glycine is added as a solid. Preferably, the added glycine is in free-base form. Preferably, the resulting concentration of glycine in the alkaline peptide solution is about 5 mM to about 250 mM. Ranges of more preferred glycine concentration are about 10 mM to about 150 mM, about 20 mM to about 100 mM, about 40 mM to about 80 mM and about 55 mM to about 65 mM. Most preferably, the glycine concentration is about 60 mM.

Optionally, the pH of the alkaline peptide solution may be readjusted after the addition of the glycine. If the pH is adjusted, it is preferably adjusted to a pH between about 9.0 and about 11.0. More preferably, it is adjusted to a pH between about 9.2 and about 9.8. Most preferably, it is adjusted to about pH 9.5.

Optionally, the alkaline peptide solution with added glycine may be filtered. Filtration is recommended if any evidence of undissolved particles, dust or lint is apparent in the solution. If desired, this is also a good place in the process at which the solution can be sterilized by performing an aseptic filtration step. Preferably, the filtration will be conducted using a sterile non-pyrogenic filter having low-protein binding and a pore size of 0.45 μm or less. Preferably, the filter is a sterile non-pyrogenic, low-protein binding filter of pore size 0.22 μm or less. More preferably, the filter is a sterile 0.22 μm Millex® filter (Millipore Corporation, Waltham, Mass., USA).

The next step in the process of forming crystals is addition to the alkaline peptide solution of about 2% to about 20% of the total final volume of an alcohol selected from the group consisting of ethanol and isopropanol, and about 0.5 moles to about 2.5 moles of zinc per mole of the peptide. The zinc and ethanol may be added in a single aqueous stock solution or may be added separately in one or more steps in any order. Preferably, the alcohol is added before the zinc is added.

Preferably, the added alcohol represents, by volume, about 2% to about 20% of the total final volume of the alkaline peptide-zinc-alcohol solution. More preferably, the alcohol represents about 5% to about 15% of the total final volume. More preferably, the alcohol represents about 6% to about 12% of the total final volume. Most preferably, the alcohol represents about 9% of the total final volume. Preferably, the alcohol is ethanol.

The zinc added at this stage refers to the zinc ion. The zinc may be added in a variety of forms, but a zinc oxide solution acidified with dilute HCl and salt forms such as zinc acetate or zinc chloride are preferred. More preferred is a zinc oxide solution acidified with dilute HCl.

Preferably, 1.0 moles to about 2.25 moles of zinc per mole of the peptide is added in this process step. Other preferred ranges of zinc addition include 1.1 to 2.0 moles of zinc per mole of the peptide, 1.3 to 1.7 moles per mole of peptide, and 1.4 to 1.6 moles per mole of peptide. Most preferably, about 1.5 moles of zinc per mole of peptide is added.

Preferably, the solution comprising zinc that is added to the peptide solution is added slowly and/or in small increments, which minimizes the localized precipitation of peptide and/or zinc complexes that may form at the site of addition. More preferably, glycine is also a component of the solution comprising zinc that is being added at this step. For example, a zinc-glycine solution may be prepared by dissolving zinc oxide in dilute HCl to a pH of about 1.6 and then adding solid glycine. A sufficient quantity of glycine is added to raise the pH of the solution to between about pH 2 and about pH 3. The pH of the zinc-glycine solution may be raised further using, for example, dilute NaOH. A preferred pH range of the zinc-glycine solution is about pH 4.0 to about pH 6.0. A more preferred pH range of the zinc-glycine solution is about pH 5.0 to about pH 5.5. As noted earlier, glycine has a binding affinity for zinc that may compete with zinc binding to the peptide. Thus, the presence of glycine in the solution comprising zinc that is being added to the composition allows the zinc solution to be added more quickly because localized precipitation problems are minimized. In addition, having a zinc-glycine solution above pH 2.0, and preferably about pH 4.0 to about pH 6.0, allows the solution to be sterile filtered using filters that are rated by their manufacturers to handle, for example, pH 2-10 solutions, prior to its introduction into a sterile peptide composition. Preferably, the zinc-glycine solution comprises about 50 mM to about 70 mM glycine and about 20 mM to about 200 mM zinc.

The last steps in the initial crystallization of a selected peptide are adjusting the pH of the solution to between about pH 7.5 and about pH 10.5 and allowing crystals of the peptide to form. Preferred reagent solutions useful for adjusting the pH of the solution include dilute HCl, dilute acetic acid and dilute NaOH.

Preferred pH ranges for crystallization of selected peptides include about pH 8.0 to about pH 10.0, about pH 7.5 to about pH 9.5, about pH 8.5 to about pH 9.2, about pH 9.0 to about pH 9.5, about pH 7.5 to about pH 8.5, about pH 8.7 to about pH 9.5, and about pH 9.2 to about pH 10.0.

One skilled in the art will recognize that the preferred pH of crystallization will depend on many factors, including the nature of the peptide and its concentration, the alcohol concentration, the zinc concentration, the ionic strength of the solution and the temperature of crystallization. By way of illustration, the peptide $Val^8$-$Glu^{30}$-GLP-1(7-37)OH produced crystals at only select ethanol and zinc concentrations at a pH range of about 7.7 to about 8.1, whereas the peptide $Val^8$-$His^{37}$-GLP-1(7-37)OH produced crystals over a broad range of zinc and ethanol concentrations at a pH range of about 9.8 to about 10.4.

The skilled artisan will further recognize that, for a given set of conditions, a preferred manner of determining the optimal pH of crystallization is to determine it empirically, that is, to slowly add the acidification solution, preferably dilute HCl or dilute acetic acid, in small increments, and observe what happens after each increment is added. Generally, small quantities of localized zones of precipitation will occur at the spot of addition of the acidic solution. When gentle swirling takes increasingly longer periods of time to completely redissolve the precipitation, that is the best time to stop adding the acid and allow crystallization from the clear or slightly cloudy solution to proceed.

The skilled artisan will further recognize that the pH and temperature that one selects for crystallization will have an impact on the speed at which the crystallization proceeds, the crystallization yield, and the size and homogeneity of the crystals formed. Preferably, the pH of crystallization for the selected peptides is about pH 8.0 to about pH 10. More preferably, the pH is about 8.7 to about 9.5. Other ranges of preferred pH of crystallization are about 8.8 to about 9.3, about 9.0 to about 9.5, and about 8.5 to about 9.3. Most preferably, the crystallization is conducted at about pH 9.1.

Preferably, the temperature of crystallization is about 10° C. to about 30° C. More preferably, the temperature of crystallization is about 15° C. to about 28° C. Most preferably, the temperature of crystallization is ambient temperature, or about 20° C. to about 25° C.

Preferably, the crystallization step described above is complete, that is, 90% or more of the peptide is precipitated in predominantly crystalline form, in about 3 hours to about 72 hours. More preferably, the crystallization is complete in about 10 hours to about 48 hours. Most preferably, the crystallization is complete in about 16 hours to about 26 hours. Completion of crystallization may be determined by a variety of means, including HPLC analysis of the peptide present in an aliquot of the composition. Method 5 herein describes one such protocol that may be employed.

Preferably, the crystals produced according to the steps of the process described above are thin plate crystals. The crystals produced by the process may be examined by microscopy.

Pharmaceutical compositions comprising crystals of a GLP-1 peptide prepared as described above may be prepared by adding suitable, pharmaceutically acceptable excipients to the crystal suspension in the original mother liquor. Alternatively, the crystals may be isolated by filtration, gentle centrifugation or other means of phase separation, and used in a variety of ways to prepare pharmaceutically acceptable compositions. The skilled artisan will recognize suitable procedures and excipients useful for preparing such pharmaceutical compositions.

The following process starts with the crystals and original mother liquor from the initial crystallization stage and continues with the preparation of a stable pharmaceutical composition.

To prepare a stable pharmaceutical composition of crystals of a selected peptide, the pH of the suspension of crystals in their complete original mother liquor, or portion thereof, is lowered to a pH value at which 97% or more of the peptide becomes insoluble. Preferably, this part of the process begins within a few hours after the initial crystallization is determined to be complete. Preferably, the pH is lowered using a dilute solution of HCl or acetic acid wherein the acidic solution is added slowly and in incremental portions. The skilled artisan will recognize that the preferred pH at which this second stage of crystallization should occur will depend on many factors, including the nature of the peptide and its concentration, the alcohol concentration, the zinc concentration, the ionic strength of the suspension and the temperature of crystallization. Preferably, the pH is about 0.2 to 2.0 pH units lower than the pH at which the initial crystallization proceeded. More preferably, the pH is about 0.5 to about 1.5 pH units lower, and most preferably, the pH is about 0.8 to 1.3 pH units lower than the pH at which the initial crystallization proceeded. The temperature of this second stage of crystallization is preferably ambient temperature, or about 20° C. to about 25° C. For the peptide $Val^8$-GLP-1(7-37)OH, a preferred pH is about 7.5 to about 8.5. A more preferred pH is about 7.8 to about 8.2.

Preferably, the pH of a suspension of peptide crystals is lowered to a pH at which 98% or more, and more preferably at which 99% or more of the peptide becomes insoluble in the composition. The additional precipitation formed in this second stage of crystallization comprises crystals. Preferably, the additional precipitation formed in this second stage of crystallization will be predominantly crystals of comparable morphology and size distribution as those formed in the first stage of crystallization.

Preferably, the second stage of crystallization is complete enough, that is, 97% or more of the peptide is insoluble, to allow the following step to begin within 30 hours, more preferably within 18 hours, more preferably within 6 hours and most preferably within 2 hours of when the second stage of crystallization started. Quantitation of precipitation yield may be determined by a variety of means, including HPLC analysis of the peptide present in an aliquot of the composition.

The next step in the process to prepare a stable pharmaceutical composition of crystals of a selected peptide is to add a pharmaceutically acceptable preservative and a buffer selected from the group consisting of TRIS, maleate, phosphate, succinate, glycylglycine and adipate. Optionally, one or more tonicity agents such as sodium chloride, other salts, glycerin or mannitol may also be added. These components may be added as a single solution, as combination solutions or individually in any order. It is preferred that the preservative is added last. Of these components, a preferred buffer is selected from the group consisting of TRIS and maleate, a preferred preservative is m-cresol and a preferred tonicity agent is sodium chloride. A more preferred buffer is TRIS.

A preferred quantity of TRIS to add to the crystalline peptide suspension, if TRIS is the selected buffer, is such that the TRIS concentration in the final composition is about 5 mM to about 40 mM. A more preferred range of TRIS concentration in the final composition is about 10 mM to about 20 mM. A most preferred concentration of TRIS in the final composition is about 15 mM.

A preferred quantity of maleate to add to the crystalline peptide suspension, if maleate is the selected buffer, is such that the maleate concentration in the final composition is about 2 mM to about 20 mM. A more preferred range of maleate concentration in the final composition is about 5 mM to about 15 mM. A most preferred concentration of maleate in the final composition is about 9 mM.

If sodium chloride is selected to be a component of the peptide composition, a preferred quantity to add to the crystalline peptide suspension is such that the added sodium chloride in the final composition is about 30 mM to about 200 mM. A more preferred concentration of added sodium chloride in the final composition is 50 mM to about 150 mM. Other ranges of preferred sodium chloride concentration are about 80 mM to about 120 mM, about 70 mM to about 130 mM, and about 90 mM to about 130 mM. A most preferred quantity of added sodium chloride in a pharmaceutical composition is about 110 mM.

Although any pharmaceutically acceptable preservative may be added to the crystalline peptide suspension at this point in the process, for a composition of the present invention a phenolic preservative or benzyl alcohol is preferred. Examples of phenolic preservatives include phenol, chlorocresol, m-cresol, o-cresol, p-cresol, ethylparaben, methylparaben, propylparaben, butylparaben, thymol or mixtures thereof. More preferred preservatives are benzyl alcohol, m-cresol, phenol, methylparaben and mixtures thereof. A most preferred pharmaceutically acceptable preservative is m-cresol.

A preferred quantity of a pharmaceutically acceptable preservative to add to a crystalline peptide composition at this point in the process is an amount such that the preservative concentration in the final composition is about 1.0 mg/mL to about 20.0 mg/mL. More preferred ranges of concentration of preservative in the final composition are about 2.0 mg/mL to about 8.0 mg/mL, about 2.5 mg/mL to about 4.5 mg/mL and about 2.0 mg/mL to about 4.0 mg/mL. A most preferred concentration of preservative in the final composition is about 3.0 mg/mL.

The final step in the process of preparing a stable pharmaceutical composition of crystals of a selected peptide is an adjustment to a final pH between about 6.0 and about 8.5 and preferably between about pH 6.5 and about pH 8.0. Although any of a wide variety of acidification and/or alkalization reagent solutions may be employed for this pH adjustment, dilute HCl, dilute NaOH and dilute acetic acid are preferred. More preferred reagent solutions are dilute HCl and dilute NaOH. The preferred pH to which the composition is adjusted will depend to some extent upon the selected peptide, the peptide concentration, the proposed route of administration and the selected buffer.

Preferably, with TRIS as the selected buffer, the pH will be adjusted to a pH between about 6.5 and about 8.5. More preferably, the pH will be adjusted to a pH between about 7.0 and about 7.8, between about 7.2 and about 7.8, between about 7.5 and about 8.5, or between about 7.0 and about 8.0. A most preferred pH to which the composition is adjusted when TRIS is the selected buffer is about 7.5. With maleate as the selected buffer, the pH will be adjusted to a pH between about 6.0 and about 7.5. More preferably, the pH will be adjusted to a pH between about 6.4 and about 7.5, between about 6.4 and about 7.0, or between about 6.0 and about 7.0. A most preferred pH to which the composition is adjusted when maleate is the selected buffer is about 6.5.

Instead of a formulation approach, long acting GLP-1 compounds suitable for the treatment regimen of the present invention can be derivitized. Derivatization is accomplished by various means. Modifications at amino acid side groups include, without limitation, acylation of lysine s-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist. The α-carbon of an amino acid may be mono- or dimethylated.

Preferred GLP-1 derivatives are achieved through acylation. Using the principle of fatty acid derivitization, GLP-1 action is protracted by facilitating binding to plasma albumin via association of the fatty acid residue to fatty acid binding sites on albumin in the blood and peripheral tissues. A preferred GLP-1 derivative is $Arg^{34}Lys^{26}$-(N-ε-(γ-Glu(N-α-hexadecanoyl)))-GLP-1(7-37). GLP-1 derivatives and methods of making such derivatives are disclosed in Knudsen, et al. (2000) *J. Med. Chem*. 43:1664-1669. In addition, numerous published applications describe derivatives of GLP-1, GLP-1 analogs, Exendin-4, and Exendin-4 analogs. See U.S. Pat. No. 5,512,540, WO96/29342, WO98/08871, WO99/43341, WO99/43708, WO99/43707, WO99/43706, and WO99/43705.

GLP-1 peptides can also be encapsulated using microspheres and then delivered orally. For example, GLP-1 compounds can be encapsulated into microspheres composed of a commercially available, biocompatible, biodegradable polymer, poly(lactide-co-glycolide)-COOH and olive oil as a filler. See Joseph, et al. (2000) *Diabetologia* 43:1319-1328. Other types of microsphere technology is also available commercially such as Medisorb® and Prolease® biodegradable polymers from Alkermes. Medisorb® polymers can be produced with any of the lactide isomers. Lactide:glycolide ratios can be varied between 0:100 and 100:0 allowing for a broad range of polymer properties. This allows for the design of delivery systems and implantable devices with resorption times ranging from weeks to months.

Another embodiment of the present invention encompasses articles of manufacture for human pharmaceutical use comprising a package insert, a container, and said insert describing a treatment regimen which involves maintaining plasma levels of a GLP-1 compound with a particular potency within a certain range that avoids or minimizes side effects such as nausea and vomiting.

The container used in the present article of manufacture is conventional in the pharmaceutical arts. Generally, the container is a vial or cartridge, usually made of glass, and accompanying cap, closure, bead, plunger, septum, and/or seal or other such article suitable for use by the patient or pharmacist. Alternatively, the container is part of a kit consisting of a cartridge containing dried powder and a syringe pre-filled with an appropriate diluent. Other options include the container consisting of a dual chamber cartridge with a bypass that keeps the diluent liquid and the dried powder separate from each other until reconstitution is desired. At the time of reconstitution, the dual chamber cartridge permits the diluent liquid to flow into the dried powder. Preferably, the container is sized to accommodate 0.1 to 100 mL, preferably 0.5 to 25 mL, and more preferably, 5 to 10 mL, even more preferably 1.5 to 3 mL volumes. Alternatively, the container is a blister, capsule, or blister disc. Other options for the container include a transdermal patch, implantable device, microsphere carriers and other depot delivery systems.

The insert may provide the physician with a choice of several doses which result in plasma levels of the GLP-1 compound within the ranges described herein, or preferably the insert will provide the physician with a single dose which results in plasma levels of the GLP-1 compound within the ranges described herein.

The package insert provides a description of how to administer a pharmaceutical product, along with the safety and efficacy data required to allow the physician, pharmacist, and patient to make an informed decision regarding the use of the product. The package insert generally is regarded as the label of the pharmaceutical product.

The package insert may provide some or all of the following indications or label descriptions:
1) improved glycemic control in patients inadequately controlled on single or multiple oral anti-diabetic agents as a monotherapy or as a combination therapy with single of multiple oral anti-diabetic agents compared to such agents alone;
2) use for patients with inadequately controlled hyperglycemia;
3) mean reduction in HbAlc greater than or equal to 0.5%, preferably greater than or equal to 1% in patients inadequately controlled on single or multiple oral anti-diabetic agents;
4) mean weight gain for patients on monotherapy will be less than the mean weight gain for patients treated with either a TZD or sulfonylurea as monotherapy over a 3 month period or a longer period;
5) statistically significant demonstration of weight loss;
6) no severe hypoglycemia at therapeutic dose;
7) no symptomatic hypoglycemia at therapeutic dose;
8) no fixed injection meal interval;
9) initiation of daily dosing requires no more than moderate dose titration (less than or equal to 4 doses) with subsequent daily dosing independent of blood glucose monitoring;
10) at least 12 months, preferably at least 18 months refrigerated shelf-life;
11) room temperature in-use storage;
12) minimal injection site discomfort at therapeutic dose;
13) no injection site discomfort at therapeutic dose;
14) minimal nausea at therapeutic dose;
15) β cell preservation in animal models;
16) β cell preservation in humans;
17) injection volume between 0.1 and 0.25 mLs; and
18) safe for use in children.

Furthermore, the package insert may provide instructions regarding the treatment regimen encompassed by the present invention involving maintaining continuous plasma levels of GLP-1 within a therapeutic range regardless of the patient's body weight or body mass index, sex, or age. In addition, the package insert describes how the present invention provides a means to maintain steady state GLP-1 levels with a protocol that does not require the patient to self-monitor glucose levels, and that does not need to be timed with meals thereby allowing patient convenience while safely maintaining optimal blood glucose control.

Incidences of side effects are notably reduced due to the presently claimed article of manufacture providing a chronic dosing regimen. Therefore, the preferred article of manufacture provides a package insert having reported incidences of nausea in less than 30% of patients with plasma levels within the ranges described herein. More preferably, nausea and vomiting occurs in less than 20% of patients with plasma levels within the ranges described herein. Even more preferably, less than 10% of patients with plasma levels within the ranges described herein experience such side effects. Most preferably, nausea and vomiting occur in less than 5% of patients with plasma levels within the ranges described herein.

Incidences of hypoglycemia due to the treatment regimen described herein are rare. The package insert having reported incidences of hypoglycemia characterized by a blood glucose level less than 63 mg/dL is less than 10%, preferably less than 5%, and most preferably there are no reports of hypoglycemia.

The invention is illustrated by the following examples which are not intended to be limiting in any way.

EXAMPLE 1

Clinical Study in Type 2 Diabetics

Four groups of eight type 2 diabetic patients were treated with a long-acting formulation of $Val^8$-GLP-1(7-37)OH. The first three groups received either 2.5 or 3.5 or 4.5 mg once a day for 6 days. The fourth group received 4.5 mg once per day for 21 days. On the day before the study, each patient received a saline injection as placebo. Blood glucose was followed for 13 hours. All meals during the evaluation days were strictly standardized. Patients were outpatients except for the Day 6 and Day 21 evaluations over 24 hours. Following the injection on Day 1, blood samples were taken for glucose and $Val^8$-GLP-1(7-37)OH plasma levels during 4 hours. Patients were dosed each morning. On the sixth day of dosing (and also Day 21 for Group 4), samples were collected up to 26 hours post dose for the blood glucose and $Val^8$-GLP-1(7-37)OH plasma level determinations. $Val^8$-GLP-1(7-37)OH plasma levels are represented in FIGS. 1 and 3 and corresponding glucose levels are represented in FIGS. 2 and 4. Patients in the 21 day dosing group lost an average of 2.125 kg (standard deviation: 1.36 kg). Five subjects lost a total of 3 kg, one lost 2 kg, and 2 lost no weight.

EXAMPLE 2

Determination of $Val^8$-GLP-1(7-37)OH Plasma Levels

Due to the presence of endogenous concentrations of native GLP-1 peptides and degradation products such as GLP-1

(9-37)OH by DPP-IV, concentrations of intact Val$^8$-GLP-1 (7-37)OH were measured using an ELISA assay in which full-length non-degraded Val$^8$-GLP-1(7-37)OH is specifically recognized. Immunoreactive Val$^8$-GLP-1(7-37)OH is captured from the plasma by an N-terminal anti-Val$^8$-GLP-1(7-37)OH specific antisera immobilized onto a microtiter plate. This antisera is highly specific to the N-terminus of Val$^8$-GLP-1(7-37)OH. An alkaline-phosphatase conjugated antibody, specific for the C-terminus of GLP-1, is added to complete the "sandwich." Detection is completed using pNPP, a colormetric substrate for alkaline phosphatase. The amount of color generated is directly proportional to the concentration of immunoreactive Val$^8$-GLP-1(7-37)OH present in the sample. Quantitation of Val$^8$-GLP-1(7-37)OH in human plasma can be interpolated from a standard curve using Val$^8$-GLP-1(7-37)OH as the reference standard. Data was analyzed by a computer program using a weighted 4-parameter logistic algorithm. The concentration of immunoreactive Val$^8$-GLP-1(7-37)OH in test samples was determined using a standard curve.

EXAMPLE 3

In Vitro Potency Assay

HEK-293 Aurora CRE-BLAM cells expressing the human GLP-1 receptor are seeded at 20,000 to 40,000 cells/well/100 μl into a 96 well black clear bottom plate. The day after seeding, the medium is replaced with plasma free medium. On the third day after seeding, 20 μl of plasma free medium containing different concentrations of GLP-1 agonist is added to each well to generate a dose response curve. Generally, fourteen dilutions containing from 3 nanomolar to 30 nanomolar GLP-1 compound were used to generate a dose response curve from which EC50 values could be determined. After 5 hours of incubation with GLP-1 compound, 20 μl of β-lactamase substrate (CCF2-AM—Aurora Biosciences—product code 100012) was added and incubation continued for 1 hour at which point the flourescence was determined on a cytoflour.

EXAMPLE 4

Crystallization of GLP-1(7-37)OH

GLP-1(7-37)OH was dissolved in about 0.5 mL of 0.015 N NaOH at a concentration of about 17 mg/mL, based on the mass of the peptide. The protein solution was adjusted to about pH 10.5 with dilute NaOH. The solution was held at ambient temperature for about 1 hour.

To a 390 μL aliquot of this peptide solution was added 25 μL of a 1.0 M glycine pH 10 solution, giving a final concentration of about 16 mg/mL of GLP-1(7-37)OH and about 60 mM glycine. The pH of the solution was adjusted to about pH 10 with dilute HCl and/or dilute NaOH as needed.

The solution was then filtered into a glass vial through a sterile 0.22 μm Millex®-GV (Millipore Corporation, Waltham, Mass., USA) 4 mm filter unit that had been pre-rinsed with 60 mM glycine buffer at pH 10.

To 300 μL of the filtered peptide solution was added 66 μL of a 50% ethanol solution in water. To this solution was added, in small increments, a total of 14.1 μL of a 150 mM zinc oxide pH 2.3 solution (prepared with dilute HCl), with mixing by hand performed after each increment was added until the solution became clear. The molar ratio of zinc:peptide was about 1.5:1.

The final solution was adjusted to about pH 9.0 and crystallization proceeded at ambient temperature. The crystallization solution comprised about 12.6 mg/mL GLP-1(7-37)OH, 47 mM glycine, 8.7% ethanol by volume, and about 1.5 moles of zinc per mole of GLP-1(7-37)OH at pH 9.0.

After 1 day at ambient temperature, thin plate crystals of GLP-1(7-37)OH were observed under a microscope at 400× magnification.

The yield of crystallization was determined by using a spectrophotometer to compare the absorbance of an aliquot of the entire suspension redissolved in a 10-fold dilution of 0.01N HCl, with a similarly diluted supernatant obtained by centrifuging the suspension for about 4 minutes at 14,000×g. For this experiment, the crystallization yield was 92%.

EXAMPLE 5

Crystallization of Val$^8$-GLP-1(7-37)OH

Val$^8$-GLP-1(7-37)OH was dissolved in about 0.57 mL of 0.015 N NaOH at a concentration of about 17 mg/mL, based on the mass of the peptide. The protein solution was adjusted to about pH 10.5 with dilute NaOH. The solution was held at ambient temperature for about 1 hour.

To a 390 μL aliquot of this peptide solution was added 25 μL of a 1.0 M glycine pH 8 solution, giving a final concentration of about 16 mg/mL of Val$^8$-GLP-1(7-37)OH and about 60 mM glycine. The pH of the solution (about pH 9.0) was adjusted to about pH 9.9 with dilute HCl and/or dilute NaOH as needed.

The solution was then filtered into a 0.5 mL Eppendorf tube through a sterile 0.22 μm Millex®-GV (Millipore Corporation, Waltham, Mass., USA) 4 mm filter unit.

To 300 μL of the filtered peptide solution in a clean test tube was added 66 μL of a 50% ethanol solution in water. To this solution was added, in small increments, a total of 14.1 μL of a 150 mM zinc oxide pH 2.3 solution (prepared with dilute HCl), with mixing by hand performed after each increment was added until the solution became clear. The molar ratio of zinc:peptide was about 1.5:1.

The final solution was adjusted to about pH 8.9 and crystallization proceeded at ambient temperature. The crystallization solution comprised about 12.6 mg/mL Val$^8$-GLP-1(7-37)OH, 47 mM glycine, 8.7% ethanol by volume, and about 1.5 moles of zinc per mole of Val$^8$-GLP-1(7-37)OH at pH 8.9.

After about three days at ambient temperature, thin plate crystals of Val$^8$-GLP-1(7-37)OH were observed under a microscope at 400× magnification.

EXAMPLE 6

Crystallization of Val$^8$-GLP-1(7-36)NH$_2$

Val$^8$-GLP-1(7-36)NH$_2$ was dissolved in about 0.44 mL of 0.015 N NaOH at a concentration of about 17 mg/mL, based on the mass of the peptide. The protein solution was adjusted to about pH 10.5 with dilute NaOH. The solution was held at ambient temperature for about 1 hour.

To a 390 μL aliquot of this peptide solution was added 25 μL of a 1.0 M glycine pH 10.2 solution, giving a final concentration of about 16 mg/mL of Val$^8$-GLP-1(7-36)NH$_2$ and about 60 mM glycine.

The solution was then filtered into a glass vial through a sterile 0.22 μm Millex®-GV (Millipore Corporation, Waltham, Mass., USA) 4 mm filter unit.

To 300 μL of the filtered peptide solution in a clean glass vial was added 66 μL of a 50% ethanol solution in water. To this solution was added, in small increments, a total of 14.1 μL of a 150 mM zinc oxide pH 2.3 solution (prepared with dilute HCl), with mixing by hand performed after each increment was added until the solution became clear. The molar ratio of zinc:peptide was about 1.5:1.

The final solution was adjusted to about pH 9.85 and crystallization proceeded at ambient temperature. The crystallization solution comprised about 12.6 mg/mL Val$^8$-GLP-1(7-36)NH$_2$, 47 mM glycine, 8.7% ethanol by volume, and about 1.5 moles of zinc per mole of Val$^8$-GLP-1(7-36)NH$_2$ at pH 9.85.

After about three days at ambient temperature, microcrystals of Val$^8$-GLP-1(7-36)NH$_2$ were observed under a microscope at 400× magnification.

EXAMPLE 7

Crystallization of Val$^8$-GLP-1(7-37)NH$_2$

Val$^8$-GLP-1(7-37)NH$_2$ was dissolved in about 0.48 mL of 0.015 N NaOH at a concentration of about 17 mg/mL, based on the mass of the peptide. The protein solution was adjusted to about pH 11.1 with dilute NaOH, then to pH 10.36 with dilute HCl. The solution was held at ambient temperature for about 1 hour.

To a 390 μL aliquot of this peptide solution was added 25 μL of a 1.0 M glycine pH 10 solution, giving a final concentration of about 16 mg/mL of Val$^8$-GLP-1(7-37)NH$_2$ and about 60 mM glycine.

The solution was then filtered into a glass vial through a sterile 0.22 μm Millex®-GV (Millipore Corporation, Waltham, Mass., USA) 4 mm filter unit.

To 300 μL of the filtered peptide solution in a clean glass vial was added 66 μL of a 50% ethanol solution in water. To this solution was added, in small increments, a total of about 7 μL of a 150 mM zinc oxide pH 2.3 solution (prepared with dilute HCl), with mixing by hand performed after each increment was added until the solution became clear. The molar ratio of zinc:peptide was about 0.75:1.

The final solution was adjusted to about pH 9.8 and crystallization proceeded at ambient temperature. The crystallization solution comprised about 12.6 mg/mL Val$^8$-GLP-1(7-37)NH$_2$, 47 mM glycine, 8.7% ethanol by volume, and about 0.75 moles of zinc per mole of Val$^8$-GLP-1(7-37)NH$_2$ at pH 9.8.

After about 48 hours at ambient temperature, clusters of Val$^8$-GLP-1(7-37)NH$_2$ were observed under a microscope at 400× magnification.

---

We claim:

1. A method of treating a condition selected from the group consisting of hyperglycemia and type 2 diabetes which comprises maintaining chronic steady state plasma levels between about 60 picomoles/liter and about 200 picomoles/liter of a GLP-1 analog or derivative that binds the GLP-1 receptor and is in biologically active form having an in vitro potency within two-fold the in vitro potency of Val$^8$-GLP-1(7-37)OH wherein the GLP-1 analog or derivative is administered by subcutaneous injection to a human subject no more than once or twice every 24 hours.

2. The method of claim 1 wherein the plasma levels are maintained between about 100 picomolar and about 200 picomolar.

3. The method of claim 2 wherein the plasma levels are maintained between about 100 picomolar and about 180 picomolar.

4. The method of claim 1 wherein the GLP-1 analog or derivative is administered not more than once every 24 hours.

5. The method of claim 1 wherein the GLP-1 analog or derivative is a GLP-1 analog which is administered as a crystal suspension formulation.

6. The method of claim 1 wherein the GLP-1 analog or derivative is an acylated GLP-1 derivative.

7. The method of claim 6 wherein the acylated GLP-1 derivative is a GLP-1 analog acylated at the epsilon-amino group of lysine present at position 26.

8. The method of claim 7 wherein the acylated GLP-1 derivative is Arg$^{34}$Lys$^{26}$-(N-ε-(γ-Glu(N-α-hexadecanoyl)))-GLP-1(7-37).

* * * * *

SEQUENCE LISTING

```
<160> NUMBER OF SEQ ID NOS: 7

<210> SEQ ID NO 1
<211> LENGTH: 31
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa at position 31 is Gly or is absent.

<400> SEQUENCE: 1

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 is Ser or Gly;
<220> FEATURE:
<221> NAME/KEY: MISC_FEATURE
<222> LOCATION: (3)..(3)
<223> OTHER INFORMATION: Xaa at position 3 is Asp or Glu.

<400> SEQUENCE: 2

His Xaa Xaa Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

```
                    20              25              30
Ser Gly Ala Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine,
      beta-hydroxy-histidine, homohistidine,
      alpha-fluoromethyl-histidine or alpha-methyl-histidine;
<220> FEATURE:
<221> NAME/KEY: MISC_FEATURE
<222> LOCATION: (2)..(2)
<223> OTHER INFORMATION: Xaa at position 2 is Ala, Gly, Ser, Thr, Leu,
      Ile, Val, Glu, Asp, or Lys;
<220> FEATURE:
<221> NAME/KEY: MISC_FEATURE
<222> LOCATION: (3)..(3)
<223> OTHER INFORMATION: Xaa at position 3 is Glu, Asp, Lys, Thr, Ser,
      Arg, Trp, Phe, Tyr, or His;
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, Arg, His, or Lys;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys;
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, His, Phe, or Lys;
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys;
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, His, Pro, Arg, or Lys;
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gly, Gln, Asn, Arg, Cys, or Lys;
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, or Lys;
<220> FEATURE:
<221> NAME/KEY: MISC_FEATURE
<222> LOCATION: (15)..(15)
<223> OTHER INFORMATION: Xaa at position 15 is Glu, Asp, or Lys;
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, or Lys;
<220> FEATURE:
<221> NAME/KEY: MISC_FEATURE
```

-continued

```
<222> LOCATION: (17)..(17)
<223> OTHER INFORMATION: Xaa at position 17 is Gln, Asn, Arg, Glu, Asp,
      His, or Lys;
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
      Ile, Val, Arg, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, or Lys;
<220> FEATURE:
<221> NAME/KEY: MISC_FEATURE
<222> LOCATION: (20)..(20)
<223> OTHER INFORMATION: Xaa at position 20 is Lys, Arg, Gln, Glu, Asp,
      Trp, Tyr, Phe, or His;
<220> FEATURE:
<221> NAME/KEY: MISC_FEATURE
<222> LOCATION: (21)..(21)
<223> OTHER INFORMATION: Xaa at position 21 is Glu, Asp, Ala, His, Phe,
      Tyr, Trp, Arg, Leu, or Lys;
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, His, or Lys;
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      Ser, Thr, Arg, or Lys;
<220> FEATURE:
<221> NAME/KEY: MISC_FEATURE
<222> LOCATION: (26)..(26)
<223> OTHER INFORMATION: Xaa at position 26 is Leu, Gly, Ala, Ser, Thr,
      Ile, Val, Glu, Asp, or Lys;
<220> FEATURE:
<221> NAME/KEY: MISC_FEATURE
<222> LOCATION: (27)..(27)
<223> OTHER INFORMATION: Xaa at position 27 is Val, Gly, Ala, Ser, Thr,
      Leu, Ile, Glu, Asp, Arg, or Lys;
<220> FEATURE:
<221> NAME/KEY: MISC_FEATURE
<222> LOCATION: (28)..(28)
<223> OTHER INFORMATION: Xaa at position 28 is Lys, Arg, Glu, Asp, Asn,
      or His;
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, Arg, Trp, Tyr, Phe, Pro, His, or Lys;
<220> FEATURE:
<221> NAME/KEY: MISC_FEATURE
<222> LOCATION: (30)..(30)
<223> OTHER INFORMATION: Xaa at position 30 is Arg, Lys, Glu, Asp, Thr,
      Ser, Trp, Tyr, Phe, Gly, or His;
<220> FEATURE:
<221> NAME/KEY: MISC_FEATURE
<222> LOCATION: (31)..(31)
<223> OTHER INFORMATION: Xaa at position 31 is Gly, Ala, Ser, Thr, Leu,
      Ile, Val, Glu, Asp, His, Lys, Arg, Trp, Tyr, Phe, Gly-Pro,
      Gly-Pro-NH2, -NH2 or is deleted;
<220> FEATURE:
<221> NAME/KEY: MISC_FEATURE
<222> LOCATION: (32)..(32)
<223> OTHER INFORMATION: Xaa at position 32 is Arg, Lys, Glu, Asp, Ser,
      or His, or is deleted;
<220> FEATURE:
<221> NAME/KEY: MISC_FEATURE
<222> LOCATION: (33)..(33)
<223> OTHER INFORMATION: Xaa at position 33 is Arg, Lys, Glu, Asp, Ser,
      or His, or is deleted;
<220> FEATURE:
<221> NAME/KEY: MISC_FEATURE
<222> LOCATION: (34)..(34)
<223> OTHER INFORMATION: Xaa at position 34 is Asp, Glu, Gly, or Lys, or
      is deleted;
```

```
<220> FEATURE:
<221> NAME/KEY: MISC_FEATURE
<222> LOCATION: (35)..(35)
<223> OTHER INFORMATION: Xaa at position 35 is Phe, Trp, Tyr, Glu, Asp,
      Ala, or Lys, or is deleted;
<220> FEATURE:
<221> NAME/KEY: MISC_FEATURE
<222> LOCATION: (36)..(36)
<223> OTHER INFORMATION: Xaa at position 36 is Pro, Lys, Glu, or Asp, or
      is deleted;
<220> FEATURE:
<221> NAME/KEY: MISC_FEATURE
<222> LOCATION: (37)..(37)
<223> OTHER INFORMATION: Xaa at position 37 is Glu, Asp, Pro, or Lys, or
      is deleted;
<220> FEATURE:
<221> NAME/KEY: MISC_FEATURE
<222> LOCATION: (38)..(38)
<223> OTHER INFORMATION: Xaa at position 38 is Glu, Asp, Pro, or Lys, or
      is deleted;
<220> FEATURE:
<221> NAME/KEY: MISC_FEATURE
<222> LOCATION: (39)..(39)
<223> OTHER INFORMATION: Xaa at position 39 is Val, Glu, Asp, Ser, or
      Lys, or is deleted.

<400> SEQUENCE: 3

Xaa Xaa Xaa Gly Xaa Xaa Thr Xaa Asp Xaa Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa Xaa
            20                  25                  30

Xaa Xaa Xaa Xaa Xaa Xaa Xaa
            35

<210> SEQ ID NO 4
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (5)..(5)
<223> OTHER INFORMATION: Xaa at position 5 is Asp, Glu, Arg, Thr, Ala,
      Lys, or His;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (10)..(10)
<223> OTHER INFORMATION: Xaa at position 10 is Leu, Ser, Thr, Trp, His,
      Phe, Asp, Val, Glu, or Ala;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, Cys, or Cysteic Acid;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (18)..(18)
<223> OTHER INFORMATION: Xaa at position 18 is Glu, His, Ala, or Lys;
<220> FEATURE:
<221> NAME/KEY: MISC_FEATURE
```

```
<222> LOCATION: (20)..(20)
<223> OTHER INFORMATION: Xaa at position 20 is Asp, Lys, Glu, or His;
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: MISC_FEATURE
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (27)..(27)
<223> OTHER INFORMATION: Xaa at position 27 is Asp, Arg, Val, Lys, Ala,
      Gly, or Glu;
<220> FEATURE:
<221> NAME/KEY: MISC_FEATURE
<222> LOCATION: (28)..(28)
<223> OTHER INFORMATION: Xaa at position 28 is Glu, Lys, or Asp;
<220> FEATURE:
<221> NAME/KEY: MISC_FEATURE
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu;
<220> FEATURE:
<221> NAME/KEY: MISC_FEATURE
<222> LOCATION: (30)..(30)
<223> OTHER INFORMATION: Xaa at position 30 is Arg, Glu, or His;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, -NH2, Gly, Gly-Pro, or Gly-Pro-NH2, or is
      deleted.

<400> SEQUENCE: 4

His Xaa Glu Gly Xaa Xaa Thr Ser Asp Xaa Ser Ser Tyr Leu Glu Xaa
1               5                   10                  15

Xaa Xaa Ala Xaa Xaa Phe Ile Xaa Trp Leu Xaa Xaa Xaa Xaa Xaa
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (6)..(6)
<223> OTHER INFORMATION: Xaa at position 6 is His, Trp, Phe, or Tyr;
<220> FEATURE:
<221> NAME/KEY: MISC_FEATURE
<222> LOCATION: (10)..(10)
<223> OTHER INFORMATION: Xaa at position 10 is Leu, Ser, Thr, Trp, His,
      Phe, Asp, Val, Glu, or Ala;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, Cys, or Cysteic Acid;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (20)..(20)
```

```
<223> OTHER INFORMATION: Xaa at position 20 is Asp, Lys, Glu, or His;
<220> FEATURE:
<221> NAME/KEY: MISC_FEATURE
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, -NH2, Gly, Gly-Pro, or Gly-Pro-NH2, or is
      deleted.

<400> SEQUENCE: 5

His Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (16)..(16)
<223> OTHER INFORMATION: Xaa at position 16 is Gly, Asp, Glu, Gln, Asn,
      Lys, Arg, Cys, or Cysteic Acid;
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln;
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: MISC_FEATURE
<222> LOCATION: (24)..(24)
<223> OTHER INFORMATION: Xaa at position 24 is Ala, Glu, Asp, Ser, or
      His;
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, -NH2, Gly, Gly-Pro, or Gly-Pro-NH2, or
      is deleted.

<400> SEQUENCE: 6

His Xaa Glu Gly Thr Phe Thr Ser Asp Val Ser Ser Tyr Leu Glu Xaa
1               5                   10                  15

Xaa Ala Ala Lys Xaa Phe Ile Xaa Trp Leu Val Lys Gly Arg Xaa
            20                  25                  30

<210> SEQ ID NO 7
<211> LENGTH: 31
<212> TYPE: PRT
<213> ORGANISM: Artificial Sequence
<220> FEATURE:
```

```
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2amino-histidine, beta-hydroxy-histidine,
      homohistidine, alpha-fluoromethyl-histidine or alpha-methyl-
      histidine;
<220> FEATURE:
<221> NAME/KEY: MISC_FEATURE
<222> LOCATION: (2)..(2)
<223> OTHER INFORMATION: Xaa at position 2 is glycine, alanine, valine,
      leucine, isoleucine, serine or threonine;
<220> FEATURE:
<221> NAME/KEY: MISC_FEATURE
<222> LOCATION: (16)..(16)
<223> OTHER INFORMATION: Xaa at position 16 is aspartic acid, glutamic
      acid, glutamine, asparagine, lysine, arginine, cysteine,
      or cysteic acid;
<220> FEATURE:
<221> NAME/KEY: MISC_FEATURE
<222> LOCATION: (31)..(31)
<223> OTHER INFORMATION: Xaa at position 31 is -NH2 or Gly(OH).

<400> SEQUENCE: 7

Xaa Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Xaa
            20                  25                  30
```